United States Patent
So et al.

(10) Patent No.: US 11,701,661 B2
(45) Date of Patent: Jul. 18, 2023

(54) METHOD AND SYSTEM FOR LOCALIZED HEATING BY ILLUMINATION OF PATTERNED THIN FILMS

(71) Applicant: Kryptos Biotechnologies, Inc., Hayward, CA (US)

(72) Inventors: Austin So, Pleasanton, CA (US); Jun Ho Son, Albany, CA (US)

(73) Assignee: Kryptos Biotechnologies, Inc., Hayward, CA (US)

( * ) Notice: Subject to any disclaimer, the term of this patent is extended or adjusted under 35 U.S.C. 154(b) by 465 days.

(21) Appl. No.: 16/653,734

(22) Filed: Oct. 15, 2019

(65) Prior Publication Data

US 2020/0114361 A1 Apr. 16, 2020

Related U.S. Application Data

(60) Provisional application No. 62/746,490, filed on Oct. 16, 2018.

(51) Int. Cl.
*B01L 7/00* (2006.01)
*B01L 3/00* (2006.01)
*C12Q 1/686* (2018.01)

(52) U.S. Cl.
CPC .............. *B01L 7/52* (2013.01); *B01L 3/508* (2013.01); *C12Q 1/686* (2013.01); *B01L 2300/0809* (2013.01); *B01L 2300/12* (2013.01); *B01L 2300/1861* (2013.01)

(58) Field of Classification Search
None
See application file for complete search history.

(56) References Cited

U.S. PATENT DOCUMENTS

| | | | |
|---|---|---|---|
| 6,093,370 A | 7/2000 | Yasuda et al. | |
| 2001/0029017 A1* | 10/2001 | Yasuda | C12Q 1/6806 514/1 |
| 2009/0244893 A1 | 10/2009 | Villard | |
| 2010/0167288 A1 | 7/2010 | Gale et al. | |
| 2014/0302562 A1 | 10/2014 | Burroughs | |
| 2018/0080064 A1 | 3/2018 | Lee et al. | |

(Continued)

FOREIGN PATENT DOCUMENTS

| | | | |
|---|---|---|---|
| WO | 0241997 A1 | 5/2002 | |
| WO | WO-2017019768 A1 * | 2/2017 | ........ B01L 3/502707 |

OTHER PUBLICATIONS

PCT/US2019/056398, "International Preliminary Report on Patentability", dated Apr. 29, 2021, 9 pages.

(Continued)

*Primary Examiner* — Matthew D Krcha
(74) *Attorney, Agent, or Firm* — Kilpatrick Townsend & Stockton LLP

(57) ABSTRACT

This disclosure describes various reaction vessel configurations that include a housing component; a reaction chamber defined by the housing component; and a light absorbing layer conforming to a portion of an interior-facing surface of the housing component that defines the reaction chamber, the light absorbing layer comprising multiple discrete regions. An energy source may direct light at one or more of the discrete regions of the light absorbing layer so as to heat the discrete regions and ultimately heat a solution within a reaction chamber.

8 Claims, 18 Drawing Sheets

(56) References Cited

U.S. PATENT DOCUMENTS

2018/0236451 A1  8/2018  Lee et al.
2019/0283023 A1  10/2019 Son et al.

OTHER PUBLICATIONS

Liu et al. "Two kinds of polarization filter based on photonic crystal fiber with nanoscale gold film." EEE Photonics Journal, vol. 7, No. 1,, Feb. 2015, pp. 1-10.
Application No. PCT/US2019/056398, International Search Report and the Written Opinion, dated Jan. 10, 2020, 13 Pages.
Application No. EP19874734.7, Extended European Search Report, dated May 27, 2022, 8 pages.

* cited by examiner

METHOD AND SYSTEM FOR LOCALIZED HEATING BY ILLUMINATION OF PATTERNED THIN FILMS

CROSS-REFERENCE TO RELATED APPLICATIONS

This application claims priority to U.S. Provisional Patent Application No. 62/746,490, filed Oct. 16, 2018, entitled "METHOD AND SYSTEM FOR LOCALIZED HEATING BY ILLUMINATION OF PATTERNED THIN FILMS," the disclosure of which is hereby incorporated by reference in its entirety for all purposes.

BACKGROUND OF THE INVENTION

Reaction vessels are often used to perform various operations on DNA strands that can include operations such as polymerase chain reaction (PCR) and DNA sequencing. Polymerase chain reaction (PCR) has become an essential technique in the fields of clinical laboratories, agricultural science, environmental science, and forensic science. PCR requires thermal cycling, or repeated temperature changes between two or three discrete temperatures to amplify specific nucleic acid target sequences. To achieve such thermal cycling, conventional bench-top thermal cyclers generally use a metal heating block powered by Peltier elements. Unfortunately, this method of thermally cycling the materials within the reaction vessels can be slower than desired. At least for these reasons, alternate means that improve the speed and/or reliability of the thermal cycling are desirable.

SUMMARY OF THE INVENTION

This disclosure relates to methods, systems, and apparatus suitable for use with a reaction vessel.

A reaction vessel system is disclosed and includes the following: a reaction vessel, which may include: a housing component; a reaction chamber defined by the housing component; and a light absorbing layer conforming to a portion of an interior-facing surface of the housing component that defines the reaction chamber, the light absorbing layer comprising a plurality of discrete regions; and a first energy source (e.g., a light emitting diode configured to emit, for example, visible light, infrared light, ultraviolet A light, etc.) configured to direct light through at least a portion of the housing component at one or more discrete regions of the plurality of discrete regions of the light absorbing layer. In some embodiments, the housing component of the reaction vessel may define a channel configured to direct a solution between two or more different discrete regions of the plurality of discrete regions. In some embodiments, the plurality of discrete regions may conform with and may be arranged along different segments of the channel. In some embodiments, the light absorbing layer may include a thin metallic film formed or deposited (e.g., plated) onto the interior-facing surface of the housing component.

In some embodiments, the reaction vessel assembly may further include a second energy source. A first one of the plurality of discrete regions may be configured to receive light from the first energy source and a second one of the plurality of discrete regions may be configured to receive light from the second energy source.

In some embodiments, each discrete region of the plurality of discrete regions may be in direct contact with a solution disposed within the reaction chamber.

In some embodiments, a first discrete region may be spaced apart from a second discrete region by a first distance. In some embodiments, the first discrete region may be fluidically coupled to the second discrete region such that a solution within the reaction vessel system is not inhibited by a physical barrier from flowing between the first and second discrete regions. In some embodiments, the first energy source may be disposed in an offset position such that a larger portion of the light from the first energy source is directed toward the first discrete region than toward the second discrete region. In some embodiments, the reaction vessel assembly may include a reflector element located between a first discrete region and a second discrete region, wherein the reflector element is configured to reflect a portion of the light from the first energy source toward the first discrete region.

In some embodiments, a reaction vessel may include an inlet port for accepting a solution; a channel coupled to the inlet port through which the solution is caused to flow; a light absorbing layer comprising a plurality of discrete regions, wherein each of the discrete regions is adjacent to a segment of the channel, and wherein the discrete regions are configured to absorb light energy from an energy source. The reaction vessel may also include an outlet port for removing the solution from the reaction vessel.

In some embodiments, at least a portion of the channel is disposed within the reaction vessel in a serpentine pattern. The discrete regions may be disposed on a single surface of the reaction vessel near opposing end portions of the reaction vessel. In some embodiments, the channel may be configured to direct a portion of the solution from a first segment of the channel adjacent to a first discrete region to a second segment of the channel adjacent to a second discrete region, wherein the first discrete region may be configured to transfer a first amount of heat to the portion of the solution when the portion of the solution is in the first segment and wherein the second discrete region may be configured to transfer a second amount of heat to the portion of the solution when the portion of the solution is in the second segment. The channel may include an intervening segment between the first and second segments, wherein the intervening segment may be, for example, configured to cause the portion of the solution to be cooled when the portion of the solution is in the intervening segment. In some embodiments, the first discrete region may include a first metallic film and the second discrete region may include a second metallic film, wherein the first metallic film may be thicker than the second metallic film, and wherein the first amount of heat may be greater than the second amount of heat (e.g., because the thicker first metallic film may absorb more light energy). In some embodiments, the first metallic film may be of a first composition having a first temperature profile and the second metallic film may be of a second composition having a second temperature profile. In these embodiments, the first amount of heat may be greater than the second amount of heat (e.g., due to the difference in composition).

In some embodiments, a first segment of the channel may have a first average cross-sectional area and a second segment has a second average cross-sectional area, wherein the first average cross-sectional area is greater than the second average cross-sectional area. In these embodiments, the solution may flow through the first segment more slowly than the second segment.

In some embodiments, a reaction vessel may include an inlet port for accepting a solution into a reaction chamber, wherein the reaction chamber may be defined by one or more walls forming an outer perimeter; a light absorbing layer including a plurality of discrete regions disposed within the outer perimeter, wherein the discrete regions may be configured to absorb light energy from an energy source, and wherein the discrete regions may be fluidically coupled such that the solution is not inhibited by a physical barrier from flowing between the discrete regions. In some embodiments, the reaction vessel may also include an outlet port for removing the solution from the reaction vessel.

In some embodiments, the light absorbing layer may include a thin metallic film formed or deposited (e.g., plated) onto an interior-facing surface of the reaction vessel such that the discrete regions are configured to directly contact the solution. In other embodiments, a substrate may overlay the light absorbing layer such that the solution does not directly contact the discrete regions.

In some embodiments, the plurality of discrete regions may include a first discrete region and a second discrete region, wherein the first discrete region may include a first metallic film and the second discrete region may include a second metallic film, wherein the first metallic film is thicker than the second metallic film. In these embodiments, the first discrete region may have a different temperature profile from the second discrete region (e.g., because the thicker first metallic film may absorb more light energy). In some embodiments, the first metallic film may be of a first composition having a first temperature profile and the second metallic film may be of a second composition having a second temperature profile. In these embodiments, the first temperature profile may be different from the second temperature profile (e.g., due to the difference in composition).

In some embodiments, the reaction vessel may be defined at least in part by a top housing component and a bottom housing component, wherein the plurality of discrete regions may include a plurality of top discrete regions formed or deposited onto an interior-facing surface of the top housing component and a plurality of bottom discrete regions formed or deposited onto an interior-facing surface of the bottom housing component. A particular top discrete region may be disposed in direct opposition to a particular bottom discrete region, such that molecules in a portion of the solution may be thermally confined within an area defined by the particular top and bottom discrete regions when the particular top and bottom discrete regions are heated to a threshold temperature. In some embodiments, the top and bottom discrete regions may have different threshold temperatures. In other embodiments, the top and bottom discrete regions may have the same threshold temperature.

In some embodiments, a first discrete region of the plurality of discrete regions may be configured to bind one or more nucleotide sequences. In some embodiments, the first discrete region may be configured to bind the nucleotide sequences via weak covalent interactions. For example, the first discrete region may include a gold film, and the weak covalent interactions may include Au-thiol bonds.

In some embodiments, a method of operating a reaction vessel may include accepting a solution into the reaction vessel via an inlet port of the reaction vessel; causing the solution to flow through the reaction vessel over a plurality of discrete regions of a light absorbing layer; directing a first light at a first discrete region of the plurality of discrete regions of the light absorbing layer, causing energy from the first light to be absorbed by the first discrete region; and causing a portion of the solution adjacent to the first discrete region to be heated (e.g., via conduction or convection as the solution flows near the first discrete region).

In some embodiments, the method may further include directing a second light at a second discrete region to cause energy from the second light to be absorbed by the second discrete region. In some embodiments, the first light may be from a first light source and the second light may be from a second light source. The second light source may be set to a lower power level than the first light source. In some embodiments, the first light source may be positioned such that it is closer in proximity to the first discrete region than the second discrete region. In some embodiments, the first discrete region and the second discrete region may be disposed along a first interior-facing region of the reaction vessel. The first discrete region and the second discrete region may be fluidically coupled such that the solution is not inhibited by a physical barrier from flowing between the discrete regions.

In some embodiments, causing the solution to flow through the reaction vessel may include causing the solution to flow through a channel having a first segment adjacent to the first discrete region and a second segment adjacent to the second discrete region. The first discrete region may be spaced apart from the second discrete region.

In some embodiments, the reaction vessel may be defined at least in part by a top housing component and a bottom housing component, wherein the plurality of discrete regions may include a plurality of top discrete regions formed or deposited onto an interior-facing surface of the top housing component and a plurality of bottom discrete regions formed or deposited onto an interior-facing surface of the bottom housing component. In some of these embodiments, a particular top discrete region may be disposed in direct opposition to a particular bottom discrete region. In these embodiments, the first light may be directed at the particular top discrete region to cause the particular top discrete region to reach a first threshold temperature, and a second light may be directed at the particular bottom discrete region to cause the particular bottom discrete region to reach a second threshold temperature, such that molecules in a portion of the solution may be thermally confined within an area defined by the particular top and bottom discrete regions.

In some embodiments, one or more nucleotide sequences may be bound to the first discrete region via weak covalent interactions. For example, the first discrete region may include a gold film, and the weak covalent interactions may include Au-thiol bonds.

Other aspects and advantages of the invention will become apparent from the following detailed description taken in conjunction with the accompanying drawings which illustrate, by way of example, the principles of the described embodiments.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION OF THE INVENTION

Figure 1A:
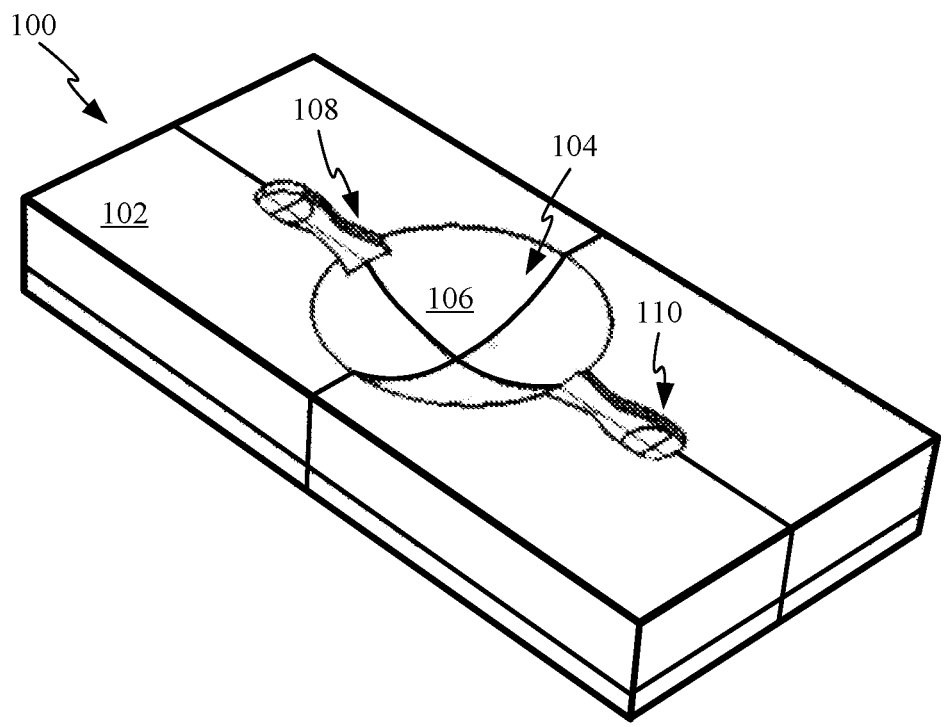
FIG. 1A shows an exemplary reaction vessel suitable for use with the described embodiments.

In the following detailed description, references are made to the accompanying drawings, which form a part of the description and in which are shown, by way of illustration, specific embodiments in accordance with the described embodiments. Although these embodiments are described in sufficient detail to enable one skilled in the art to practice the described embodiments, it is understood that these examples are not limiting; such that other embodiments may be used, and changes may be made without departing from the spirit and scope of the described embodiments.

Microfluidics systems or devices have widespread use in chemistry and biology. In such devices, fluids are transported, mixed, separated or otherwise processed. In many microfluidics devices, various applications rely on passive fluid control using capillary forces. In other applications, external actuation means (e.g., rotary drives) are used for the directed transport of fluids. "Active microfluidics" refers to the defined manipulation of the working fluid by active (micro) components such as micropumps or microvalves. Micropumps supply fluids in a continuous manner or are used for dosing. Microvalves determine the flow direction or the mode of movement of pumped liquids. Processes that are normally carried out in a laboratory can be miniaturized on a single chip in order to enhance efficiency and mobility as well to reduce sample and reagent volumes. Microfluidic structures can include micropneumatic systems, i.e., microsystems for the handling of off-chip fluids (liquid pumps, gas valves, etc.), and microfluidic structures for the on-chip handling of nanoliter (nl) and picoliter (pl) volumes (Nguyen and Wereley, Fundamentals and Applications of Microfluidics, Artech House, 2006).

Advances in microfluidics technology are revolutionizing molecular biology procedures for enzymatic analysis (e.g., glucose and lactate assays), DNA analysis (e.g., polymerase chain reaction and high-throughput sequencing), and proteomics. Microfluidic biochips integrate assay operations such as detection, as well as sample pre-treatment and sample preparation on one chip (Herold and Rasooly, editors, Lab-on-a-Chip Technology: Fabrication and Microfluidics, Caister Academic Press, 2009; Herold and Rasooly, editors, Lab-on-a-Chip Technology: Biomolecular Separation and Analysis, Caister Academic Press, 2009). An emerging application area for biochips is clinical pathology, especially the immediate point-of-care diagnosis of diseases. In addition, some microfluidics-based devices are capable of continuous sampling and real-time testing of air/water samples for biochemical toxins and other dangerous pathogens.

Many types of microfluidic architectures are currently in use and include open microfluidics, continuous-flow microfluidics, droplet-based microfluidics, digital microfluidics, paper-based microfluidics and DNA chips (microarrays).

In open microfluidics, at least one boundary of the system is removed, exposing the fluid to air or another interface (i.e., liquid) (Berthier et al., Open microfluidics, Hoboken, N.J.: Wiley, Scrivener Publishing, 2016; Pfohl et al., Chem Phys Chem. 4:1291-1298, 2003; Kaigala et al., Angewandte Chemie International Edition. 51:11224-11240, 2012). Advantages of open microfluidics include accessibility to the flowing liquid for intervention, larger liquid-gas surface area, and minimized bubble formation (Berthier et al., Open microfluidics, Hoboken, N.J.: Wiley, Scrivener Publishing, 2016; Kaigala et al., Ange. Chemie Int. Ed. 51:11224-11240, 2012; Li et al., Lab on a Chip 17: 1436-1441). Another advantage of open microfluidics is the ability to integrate open systems with surface-tension driven fluid flow, which eliminates the need for external pumping methods such as peristaltic or syringe pumps (Casavant et al., Proc. Nat. Acad. Sci. USA 110:10111-10116, 2013). Open microfluidic devices are also inexpensive to fabricate by milling, thermoforming, and hot embossing (Guckenberger et al., Lab on a Chip, 15: 2364-2378, 2015; Truckenmuller et al., J. Micromechanics and Microengineering, 12: 375-379, 2002; Jeon et al., Biomed. Microdevices 13: 325-333, 2010; Young et al., Anal. Chem. 83:1408-1417, 2011). In addition, open microfluidics eliminates the need to glue or bond a cover for devices which could be detrimental for capillary flows. Examples of open microfluidics include open-channel microfluidics, rail-based microfluidics, paper-based, and thread-based microfluidics (Berthier et al., Open microfluidics, Hoboken, N.J.: Wiley, Scrivener Publishing, 2016; Casavant et al., Proc. Nat. Acad. Sci. USA 110:10111-10116, 2013; Bouaidat et al., Lab on a Chip 5: 827, 2005).

Continuous flow microfluidics are based on the manipulation of continuous liquid flow through microfabricated channels (Nguyen et al., Micromachines 8:186, 2017; Antfolk and Laurell, Anal. Chim. Acta 965:9-35, 2017). Actuation of liquid flow is implemented either by external pressure sources, external mechanical pumps, integrated mechanical micropumps, or by combinations of capillary forces and electrokinetic mechanisms. Continuous-flow devices are useful for many well-defined and simple biochemical applications and for certain tasks such as chemical separations, but they are less suitable for tasks requiring a high degree of flexibility or fluid manipulations. Process monitoring capabilities in continuous-flow systems can be achieved with highly sensitive microfluidic flow sensors based on micro-electro-mechanical systems (MEMS) technology, which offers resolutions down to the nanoliter range.

Droplet-based microfluidics manipulates discrete volumes of fluids in immiscible phases with low Reynolds number and laminar flow regimes (see reviews at Shembekar et al., Lab on a Chip 8:1314-1331, 2016; Zhao-Miao et al., Chinese J. Anal. Chem. 45:282-296, 2017. Microdroplets allow for the manipulation of miniature volumes (μl to fl) of fluids conveniently, provide good mixing, encapsulation, sorting, and sensing, and are suitable for high throughput applications (Chokkalingam et al., Lab on a Chip 13:4740-4744, 2013).

Alternatives to closed-channel continuous-flow systems include open structures, wherein discrete, independently controllable droplets are manipulated on a substrate using electrowetting. By using discrete unit-volume droplets (Chokkalingam et al., Appl. Physics Lett. 93:254101, 2008), a microfluidic function can be reduced to a set of repeated basic operations, i.e., moving one unit of fluid over one unit of distance. This "digitization" method facilitates the use of a hierarchical, cell-based approach for microfluidic biochip design. Therefore, digital microfluidics offers a flexible, scalable system architecture as well as high fault-tolerance. Moreover, because each droplet can be controlled independently, these systems also have dynamic reconfigurability, whereby groups of unit cells in a microfluidic array can be reconfigured to change their functionality during the concurrent execution of a set of bioassays. Alternatively, droplets can be manipulated in confined microfluidic channels. One common actuation method for digital microfluidics is electrowetting-on-dielectric (EWOD) (reviewed in Nelson and Kim, J. Adhesion Sci. Tech., 26:12-17, 1747-1771, 2012). Many lab-on-a-chip applications have been demonstrated within the digital microfluidics paradigm using electrowetting. However, recently other techniques for droplet manipulation have also been demonstrated using magnetic force (Zhang and Nguyen, Lab on a Chip 17.6: 994-1008, 2017), surface acoustic waves, optoelectrowetting, mechanical actuation (Shemesh et al., Biomed. Microdevices 12:907-914, 2010), etc.

Paper-based microfluidics (Berthier et al., Open Microfluidics, John Wiley & Sons, Inc. pp. 229-256, 2016) rely on the phenomenon of capillary penetration in porous media. In order to tune fluid penetration in porous substrates such as paper in two and three dimensions, the pore structure, wettability and geometry of the microfluidic devices can be controlled, while the viscosity and evaporation rate of the liquid play a further significant role. Many such devices feature hydrophobic barriers on hydrophilic paper that passively transport aqueous solutions to outlets where biological reactions take place (Galindo-Rosales, Complex Fluid-Flows in Microfluidics, Springer, 2017).

Early biochips were based on the idea of a DNA microarray, e.g., the GeneChip DNA array from Affymetrix, which is a piece of glass, plastic or silicon substrate on which DNA molecules (probes) are affixed in an array. Similar to a DNA microarray, a protein array is an array in which a multitude of different capture agents, e.g., monoclonal antibodies, are deposited on a chip surface. The capture agents are used to determine the presence and/or amount of proteins in a biological sample, e.g., blood. For a review, see, e.g., Bumgarner, Curr. Protoc. Mol. Biol. 101:22.1.1-22.1.11, 2013.

In addition to microarrays, biochips have been designed for two-dimensional electrophoresis, transcriptome analysis, and PCR amplification. Other applications include various electrophoresis and liquid chromatography applications for proteins and DNA, cell separation, in particular, blood cell separation, protein analysis, cell manipulation and analysis including cell viability analysis and microorganism capturing.

Reaction vessels are often used to perform various types of operations on DNA strands that include polymerase chain reactions (PCR) and DNA sequencing. Reaction vessels can incorporate one or more of the microfluidics architectures listed above but it should be appreciated that reaction vessels can be larger than microfluidics devices and for that reason may not incorporate any of the microfluidics architectures describes above. Operations of the reaction vessels often include the need to make rapid changes in temperature within the reaction vessel. For example, in a PCR operation solution containing DNA strands is positioned within a reaction chamber defined by the reaction vessel. A heating element is used to thermally cycle the solution in order to breakdown and/or build up various different types of DNA. Unfortunately, conventional means of thermally cycling the solution are often slower than desired and not capable of varying a temperature of specific regions of a reaction chamber within the reaction vessel.

One solution to this problem is to position a light absorbing layer within the reaction chamber of the reaction vessel with light absorption characteristics that allow absorption of between 50 and 90% of the photonic energy in any light absorbed by the light absorbing layer. An energy source can be configured to direct light at the light absorbing layer, which efficiently absorbs energy from photons of the light directed at the light absorbing layer. The absorption of the photonic energy rapidly increases the temperature of the light absorbing layer. This energy received by the light absorbing layer is then transferred to a solution within the reaction chamber by thermal conduction.

In some embodiments, the light absorbing layer is divided into discrete regions. Dividing the light absorbing layer into discrete regions has the following advantages: (1) patterning the discrete regions into different shapes and thicknesses allows a specific spatial heating profile to be achieved within the reaction chamber of the reaction vessel; (2) optical sensors are able to take readings of solution within the reaction chamber through gaps between the discrete regions; and (3) an array of energy sources can be used to add different amounts of energy to each of the discrete regions of the light absorbing layer, thereby allowing solution within a first region of the reaction chamber to have a substantially different temperature than solution within a second region of the reaction chamber.

These and other embodiments are discussed below with reference to FIGS. 1A-6D; however, those skilled in the art will readily appreciate that the detailed description given herein with respect to these figures is for explanatory purposes only and should not be construed as limiting. In the following description, reference is made to the accompanying drawings which form a part hereof, and in which is shown by way of illustration specific embodiments in which the invention may be implemented. Terms such as "top" and "bottom" are used with reference to the orientation of the figures being described. Because components of embodiments of the present invention can be positioned in a number of different orientations, these terms are used for purposes of illustration and are not intended to be limiting.

FIG. 1A shows a perspective view of an exemplary reaction vessel 100 suitable for use with the described embodiments. In particular, reaction vessel 100 includes a housing component 102 formed from an optically transparent material that defines a reaction chamber 104. While reaction chamber 104 is depicted as having a substantially circular geometry it should be appreciated that the depicted shape of reaction chamber 104 should not be construed as limiting and other shapes such as oval, rhombic and rectangular are also possible. In some embodiments, the optically transparent material forming housing component 102 can be optically transparent to only those wavelengths of light that are used to heat reaction vessel 100. For example, the optically transparent material could be optically transparent to only select visible, infrared or ultraviolet frequencies of light. Reaction chamber 104 can be closed by a second housing component (not depicted) that encloses a liquid being heated within reaction chamber 104. In this way, DNA strands in a liquid solution within reaction chamber 104 can undergo rapid thermal cycles and at least a portion of any vaporized portion of the solution can subsequently condense back into the solution between the thermal cycles or after the thermal cycling is complete. A light absorbing layer 106 can be formed or deposited (e.g., plated) onto or otherwise adhered to an interior-facing surface of reaction chamber 104. Light absorbing layer 106 has good light absorbing properties and can be in direct contact with any liquid disposed within reaction chamber 104. For example, light absorbing layer 106 can be configured to absorb about 50-90% of the photonic energy incident to light absorbing layer 106. In some embodiments, light absorbing layer 106 can be a metal film formed from elemental gold, chromium, titanium, germanium or a gold alloy such as, e.g., gold-germanium, gold-chromium, gold-titanium, gold-chromium-germanium and gold-titanium-germanium. In some embodiments, light absorbing layer 106 can be a multilayer metal film formed from elemental gold, chromium, titanium, germanium or a gold alloy such as, e.g., gold-germanium, gold-chromium, gold-titanium, gold-chromium-germanium and gold-titanium-germanium. Light absorbing layer 106 can have a thickness of about 5-200 nm. Housing component 102 also defines inlet channel 108 and outlet channel 110, which can be used to cycle various chemicals, primers, DNA strands and other biological materials into and out of reaction chamber 104. In some embodiments, housing component 152 can have dimensions of about 7 mm by 14 mm; however, it should be appreciated that this size can vary. In some embodiments, a maximum dimension of the housing component may be less than 500 microns.

Figure 1B:
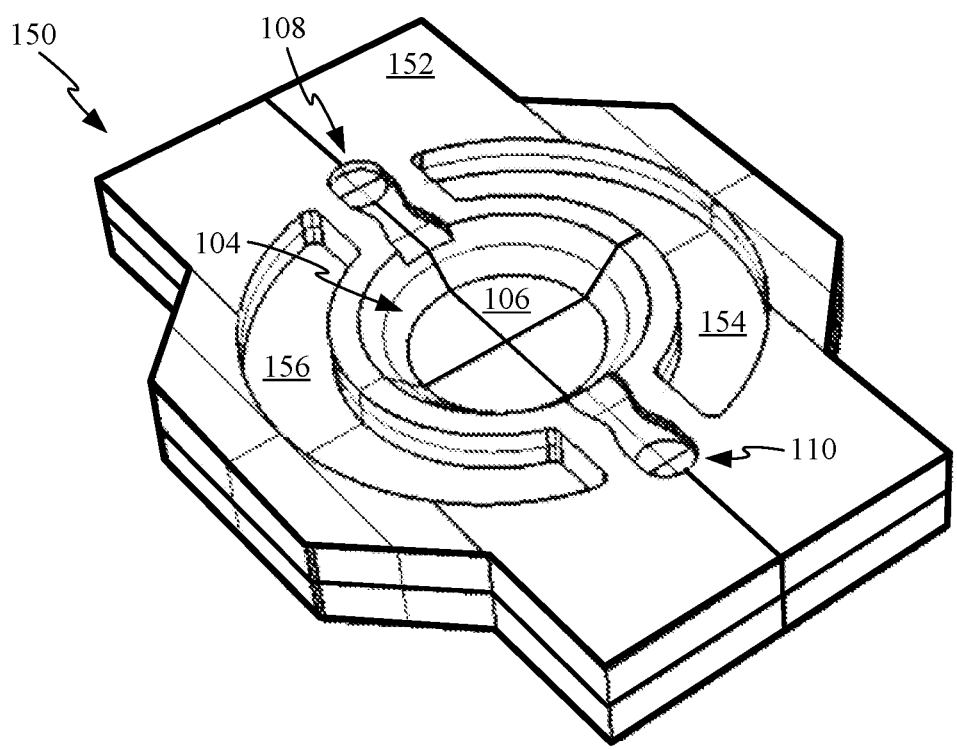
FIG. 1B shows another exemplary reaction vessel suitable for use with the described embodiments.

FIG. 1B shows a perspective view of another exemplary reaction vessel 150. Reaction vessel 150, similar to reaction vessel 100 includes housing component 152, reaction chamber 104, light absorbing layer 106, inlet channel 108 and outlet channel 110. Device housing 152 includes a widened central region that accommodates the inclusion of air gap regions 154 and 156. Air gap regions 154 and 156 can be left empty in order to discourage the lateral transmission of heat to adjacent reaction vessels. In some embodiments, the transfer of heat through air gap regions 154 and 156 can be further reduced by removing the air from air gap regions 154 and 156. In some embodiments, a diameter of housing component 152 can be about 5 mm; however, it should be appreciated that this size can vary. For example, the diameter of housing component 152 could vary from between 2 mm to 15 mm.

Figure 1C:
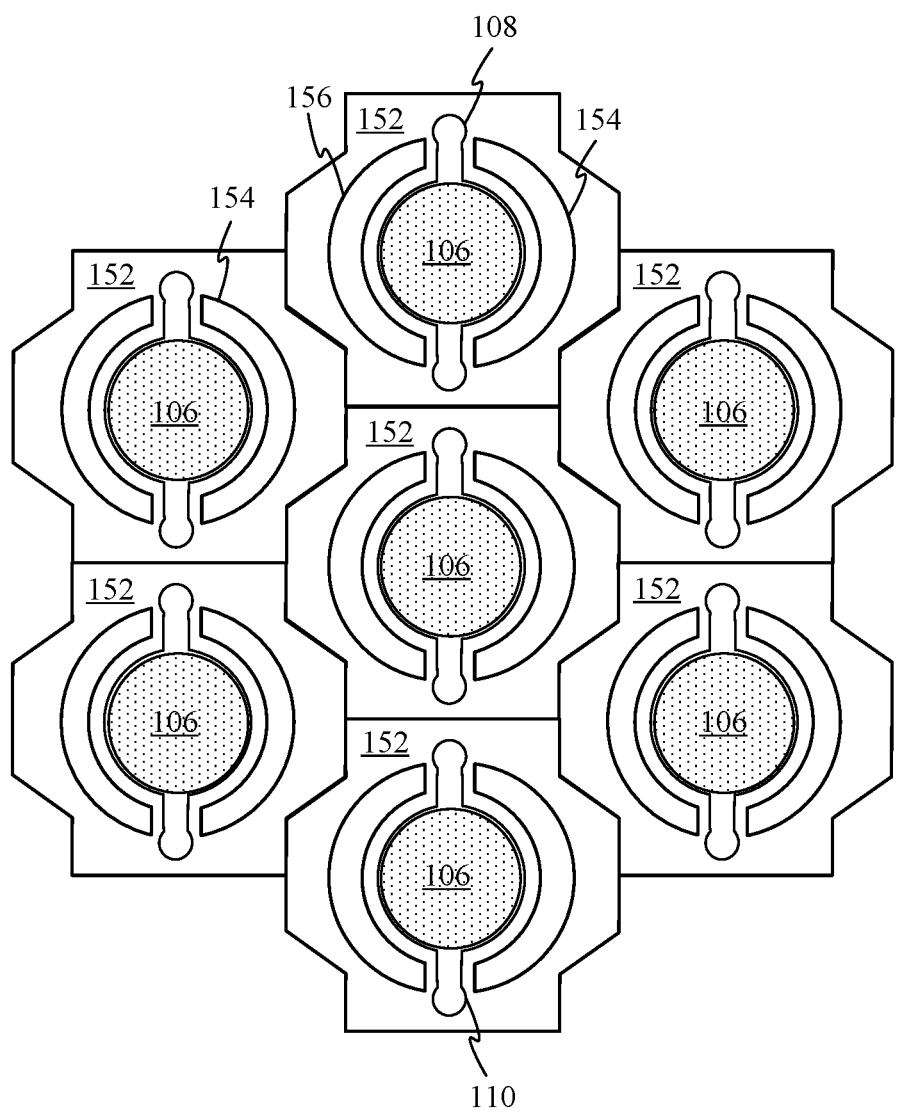
FIG. 1C shows how air gap regions establish robust barriers that reduce the lateral transfer of heat between adjacent example reaction vessels.

FIG. 1C shows how the shape of housing component 152 allow reaction vessels 150 to be packed tightly into a honeycomb or hexagonal pattern. FIG. 1C also illustrates how air gap regions 154 and 156 are able to establish robust barriers that reduce the lateral transfer of heat between adjacent reaction vessels 150. When a diameter of reaction vessel 150 is about 5 mm reaction chamber 104 can hold about 10 ul of solution and have a depth of 800 um. Generally, these devices are configured to hold between 2.5 ul and 500 ul with a depth of 200-1500 um.

Figure 2:
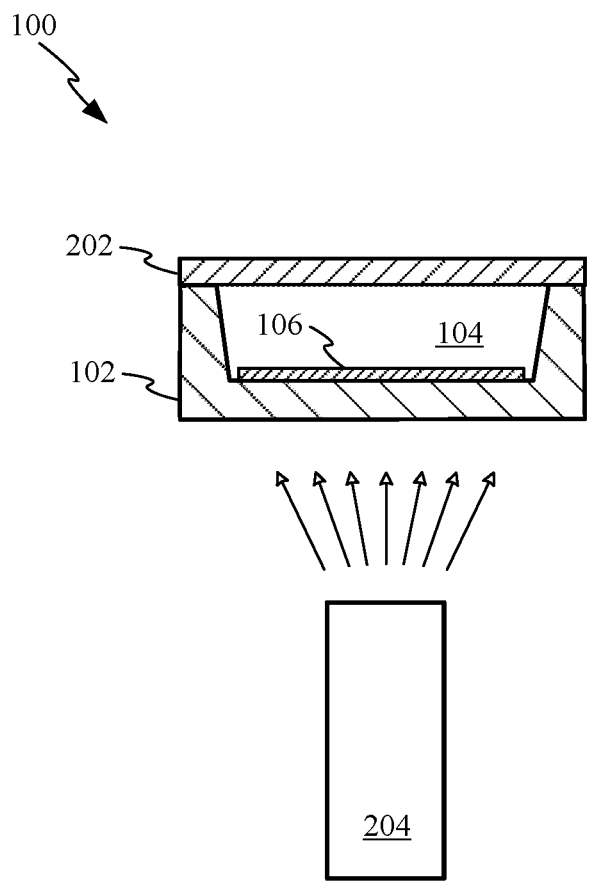
FIG. 2 shows a schematic cross-sectional side view of an example reaction vessel and how a reaction chamber can be closed.

FIG. 2 shows a schematic cross-sectional side view of an example reaction vessel 100 and how reaction chamber 104 defined by housing component 102 can be closed by housing component 202, which can take the form of a cap. In some embodiments, housing components 102 and 202 can be sealed together to prevent contamination and allow for control of other factors such as pressure within reaction chamber 104. FIG. 2 also shows energy source 204, which is configured to project light upon light absorbing layer 106. A frequency of the light projected by energy source 204 can vary. In some embodiments, energy source 204 can take the form of a light emitting diode configured to emit light with a wavelength of 450 nm, a power of 890 mW and current of 700 mA. In some embodiments, the light emitting diode may be configured to emit near infrared or ultraviolet (e.g., ultraviolet A) light. When light absorbing layer 106 is illuminated by an energy source, a large temperature difference between the hot metal surface and the cooler surrounding solution disposed within reaction chamber 104 occurs, resulting in the heating of the surrounding solution. When the energy source stops illuminating light absorbing layer 106, the resulting rapid cooling of the light absorbing layer 106 helps facilitate rapid cooling of the heated solution.

Figure 3A:
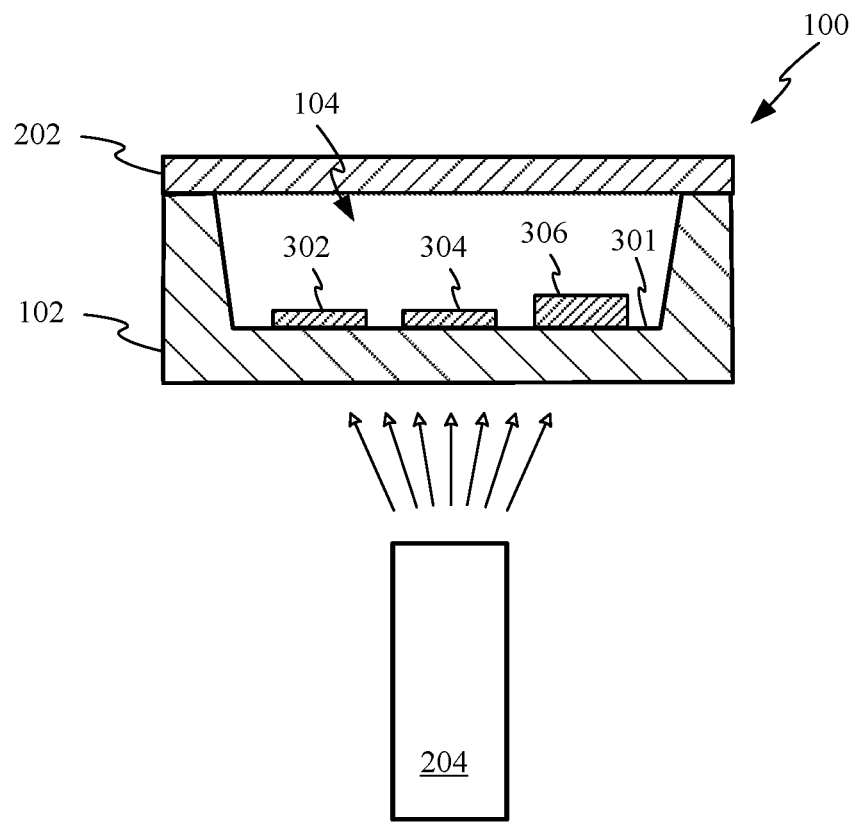
FIG. 3A shows a cross-sectional side view of an example reaction vessel and how a light absorbing layer can be separated into discrete regions.

FIG. 3A shows a cross-sectional side view of an example reaction vessel 100 and how light absorbing layer 106 can be separated into discrete regions 302, 304 and 306. These discrete regions may be superimposed on top of one or more interior-facing surfaces (e.g., the interior-facing surface 301). In some embodiments, these discrete regions can be setup to help establish a targeted amount of energy into reaction chamber 104. The gaps between regions 302, 304 and 306 reduce a total surface area across which light is received from energy source 204 compared with a light absorbing layer that extends across an entire bottom surface of reaction chamber 104. Increasing or decreasing the size of the gaps between regions 302, 304 and 306 can be used to tune the energy input into reaction chamber 104. A total area in contact with solution within reaction chamber 104 is also reduced, thereby reducing an efficiency of the transfer of heat from discrete regions 302, 304 and 306 to the solution. Gaps between regions 302, 304 and 306 also allow for optical monitoring of solution within reaction chamber 104. Gaps between regions 302, 304 and 306 may not be uniform in size allowing for some regions within reaction chamber 104 to be heated substantially more than other regions. In some embodiments, one or more of the discrete regions may have different dimensions to allow for different heating profiles. For example, as illustrated in FIG. 3A, the discrete region 306 can be thicker than discrete regions 302 and 304, thereby increasing the efficiency with which heat can be drawn into reaction chamber 104 proximate discrete region 306. As a result, all else equal (e.g., assuming the discrete regions have the same composition), the discrete region 306 in this example may absorb more energy from the energy source 204 and consequently experience a faster or greater increase in temperature than the discrete regions 302 and 304 over a given period of time. In some embodiments, one or more of the discrete regions may have different compositions, allowing for different temperature profiles. For example, referencing FIG. 3A, the discrete region 302 may be a metal film formed from elemental gold, while the discrete regions 304 and 306 may be a metal film formed from a multilayer metallic film (alternatively or additionally, these regions may be formed from a gold alloy or other suitable material). In these embodiments, all else equal (e.g., assuming uniform dimensions), the discrete regions 302 and 304 may absorb energy from the energy source 204 at a first rate, while the discrete region 306 may absorb energy from the energy source 204 at a second rate. As would be evident to one of skill in the art, the discrete regions of the reaction vessels disclosed herein allow for fine-tuned heating control, which allows for increased flexibility and a larger number of applications as compared to conventional reaction vessels. Although the reaction vessels illustrated in FIGS. 3A-3D show only three discrete regions (302, 304, 306), this disclosure contemplates any number of discrete regions each of whose dimensions and compositions may be modified as described herein.

Although the discrete regions described herein (e.g., the discrete regions 302, 304 and 306 of FIG. 3A) are separated from each other, at least for purposes of this disclosure, they are still part of a same single layer in that they are superimposed on top of the same surface (e.g., the interior-facing surface 301 of FIG. 3A). Moreover, although the thickness and/or height of the discrete regions may vary, for purposes of this disclosure, the discrete regions may nonetheless be part of the same single layer. Portions of a layer may have different thicknesses and/or heights. For example, referencing FIG. 3A, although the thickness of discrete region 306 is different from the thickness of other discrete regions (e.g., the discrete regions 302 and 304), all three discrete regions 302, 304 and 306 may be considered to be part of the same layer.

Figure 3B:
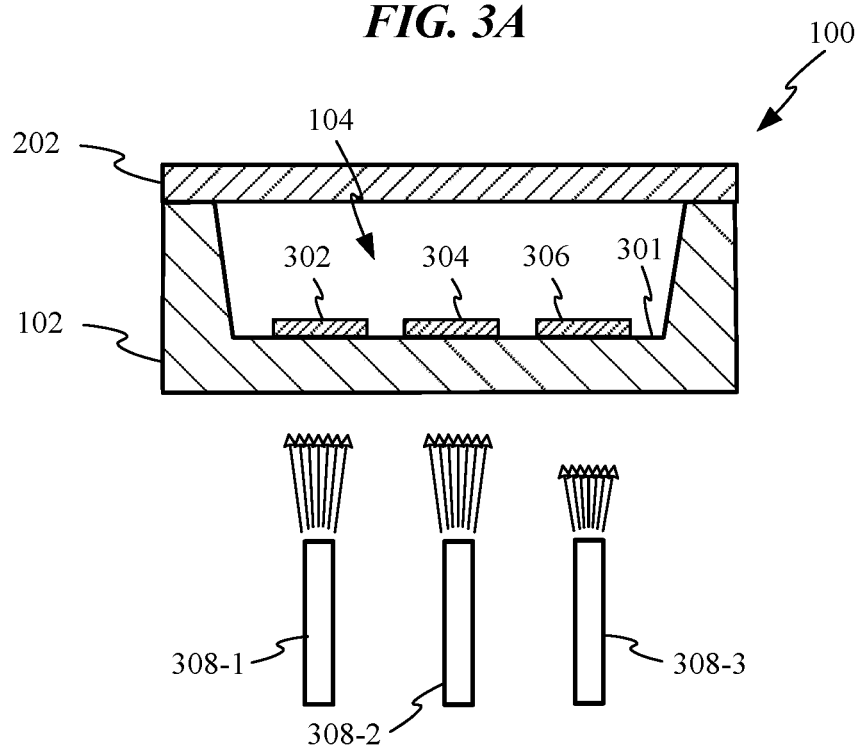
FIGS. 3B-3C show cross-sectional side views of an example reaction vessel being illuminated by an array of energy sources.

FIG. 3B shows a cross-sectional side view of another example reaction vessel 100 being illuminated by an array of energy sources 308. In some embodiments, multiple energy sources may be used to heat a reaction vessel. In some embodiments, the multiple energy sources may be arranged in an array as depicted in FIG. 3B. Referencing FIG. 3B, use of the multiple energy sources 308 can reduce an amount of light being dissipated in areas of the housing component 102 between discrete regions 302, 304 and 306 by allowing energy sources 308 to focus energy only on the discrete regions 302, 304 and 306. The use of discrete energy sources 308 may also allow for more uniform heating of each discrete region and more efficient heating overall. This may be because the energy from each energy source may be optimized to focus on one or more corresponding discrete regions, thereby ensuring that the corresponding discrete regions receive an optimal amount of the energy from the energy source. For example, referencing FIG. 3B, the energy source 308-1 may be focused on the discrete region 302 such that the entire discrete region 302 receives a maximum amount of energy from the energy source 308-1, with minimal dissipation of energy from the energy source 308-1.

In some embodiments, energy sources 308 may include specialized focusing optics to specifically target one of discrete regions 302, 304 or 306. In some embodiments, each energy source 308 of the array of energy sources 308 can be controlled separately to create a desired gradient of heat within reaction chamber 104. This degree of control may be useful in cases where, for example, different types of biological material are attached proximate to or directly on top of the discrete regions 302, 304 and 306. Because energy sources 308 can be controlled individually, the biological materials associated with a particular discrete region can be heated in accordance with a customized heating profile. For example, biological material proximate to discrete region 306 could have a substantially lower denaturing temperature than biological material proximate to discrete regions 302 and 304. As such, energy source 308-1 and 308-2 may be operated at a higher power level than the energy source 308-3, which may allow for achieving a desired denaturing temperature for both types of biological material.

Figure 3C:
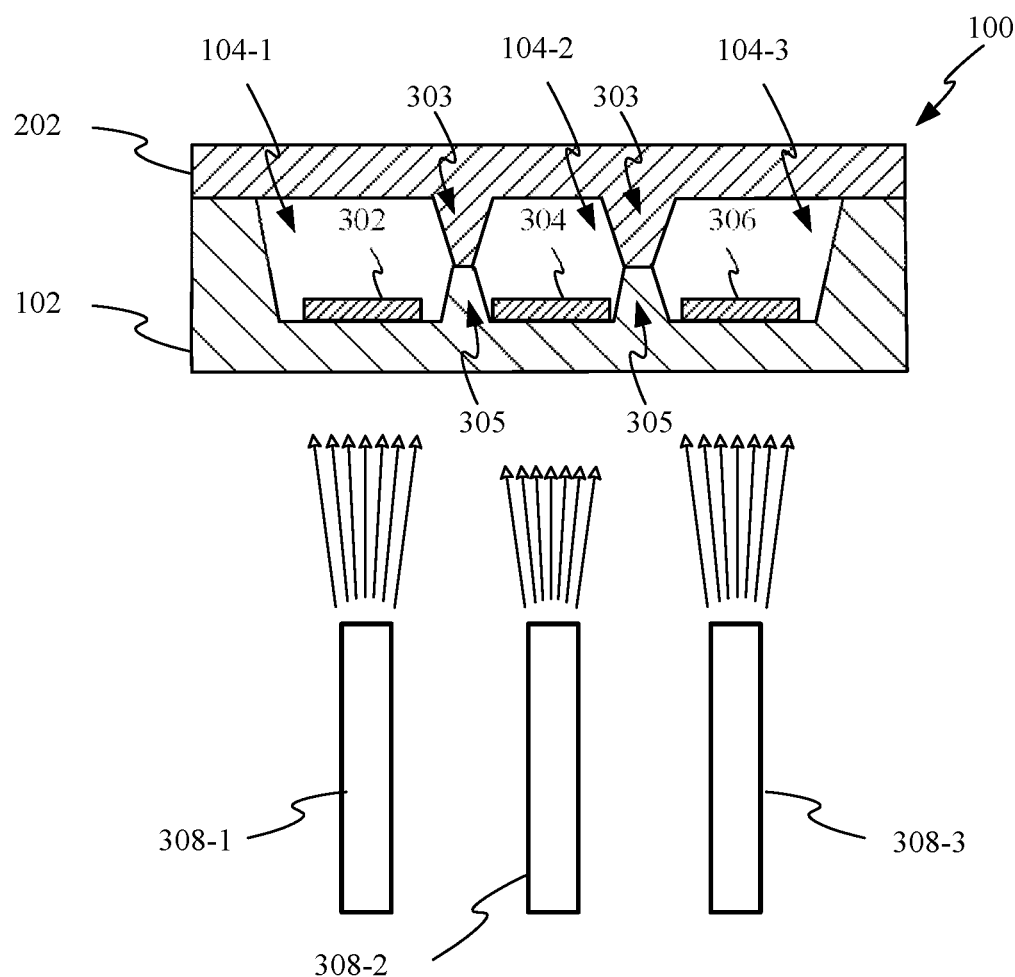

FIG. 3C shows a cross-sectional side view of an example reaction vessel 100 being illuminated by an array of energy sources 308. FIG. 3C shows how housing component 202 can include multiple protrusions or ridges 303 that meet protrusions or ridges 305 of housing component 102 to divide reaction chamber 104 into multiple smaller reaction chambers 104-1, 104-2 and 104-3. In this way, the solution within reaction chamber 104 can be separated, further improving the thermal isolation enabled by discrete regions 302, 304 and 306. While both housing components 202 and 102 are shown including respective protrusions 303 and 305, it should be appreciated that in some embodiments, protrusions 303 could extend all the way to a flat interior-facing surface of housing component 102 or protrusions 305 could extend all the way to a flat interior-facing surface of housing component 202. In some embodiments, reaction vessel 100 could include multiple different housing components 202 with different configurations of protrusions 303. For example, a housing component 202 with no protrusions could allow reactions to be carried out with a single reaction chamber 104 and in subsequent experiments or operations, the depicted housing component 202 with protrusions 303 could divide the reaction chamber into multiple smaller reaction chambers as depicted. In some embodiments, the protrusions 303 and 305 may be shaped and dimensioned to define reaction chambers of different sizes. For example, referencing FIG. 3C, the protrusions 303 and 305 are shaped and dimensioned such that reaction chamber 104-2 is smaller than reaction chambers 104-1 and 104-3. Controlling the size of reaction chambers may be used to affect the temperature profiles of the reaction chambers. For example, a relatively small reaction chamber (e.g., 104-2) may heat up more quickly than a relatively large reaction chamber (e.g., 104-1 and 104-3). In some embodiments, the energy levels of the energy sources 308 may also be varied to affect the temperature profiles of the reaction chambers. For example, as illustrated in FIG. 3C, energy source 308-2 may be operated at a lower power level than the energy sources 308-1 and 308-3.

In some embodiments, housing component 202 could include a configuration of protrusions 303 that define different-sized reaction chambers 104. For example, housing component 202 could include only one protrusion 303 defining one reaction chamber that includes both discrete regions 302 and 304 and another reaction chamber that includes only discrete region 306. In some embodiments, the configuration of protrusions 305 of housing component 102 may be adjusted for similar effects. For example, housing component 102 could include only one protrusion 305 defining one reaction chamber that includes both discrete regions 302 and 304 and another reaction chamber that includes only discrete region 306. In some embodiments, protrusions 303 and 305 may correspond to each other. Building on the previous examples, housing component 202 could include one protrusion 303 and housing component 102 could include one protrusion 305, where the protrusions 303 and 305 define one reaction chamber that includes both discrete regions 302 and 304 and another reaction chamber that includes only discrete region 306. It should be appreciated that protrusions 303 and/or 305 can include sealing elements at their distal ends that help prevent the passage of solution between adjacent reaction chambers 104.

Figure 3D:
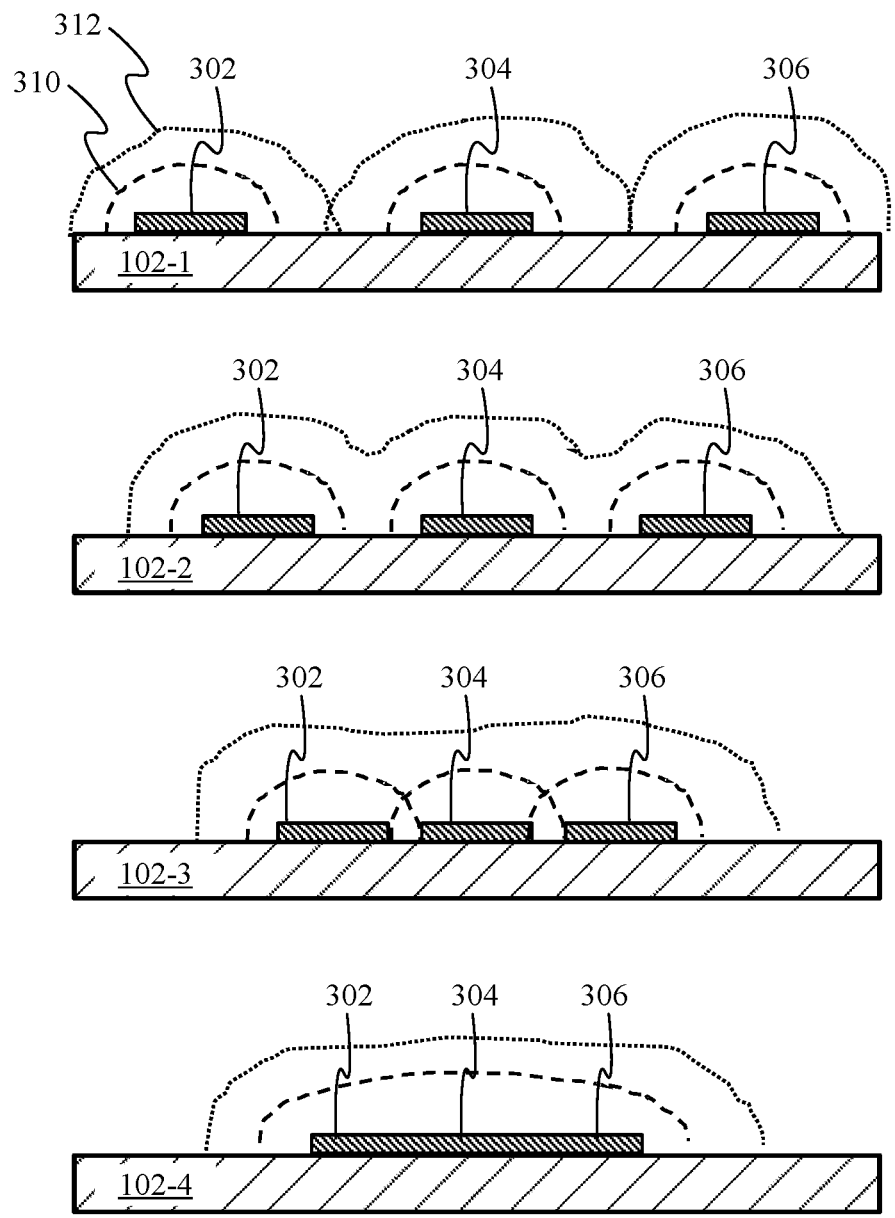
FIG. 3D shows a cross-sectional side view of a thermal profile of a portion of an example reaction vessel with different sized gaps between discrete regions of a light absorbing layer.

FIG. 3D shows a cross-sectional side view of a thermal profile of a portion of an example reaction vessel with different sized gaps between discrete regions 302, 304 and 306 of a light absorbing layer. In particular, housing component 102 is depicted with four different discrete region configurations, which are differentiated by the labels 102-1, 102-2, 102-3 and 102-4. These configurations depict two sets of contours indicative of an amount of energy or temperature change taking place in portions of the solution adjacent to discrete regions 302, 304 and 306. In particular, these depictions show how adjusting a gap size between adjacent discrete regions can change the heating profiles of a reaction chamber with a solution. Housing component 102-4 shows only a large single discrete region or alternatively a discrete region made up of regions 302, 304 and 306 in abutting contact with one another such that they effectively form a single discrete region. It should be noted that while placing discrete regions 302, 304 and 306 in abutting contact yields the largest heated area in a central portion of housing component 102-4, the peripheral ends of housing component 102 can fall below a desired temperature in some embodiments.

Figure 3E:
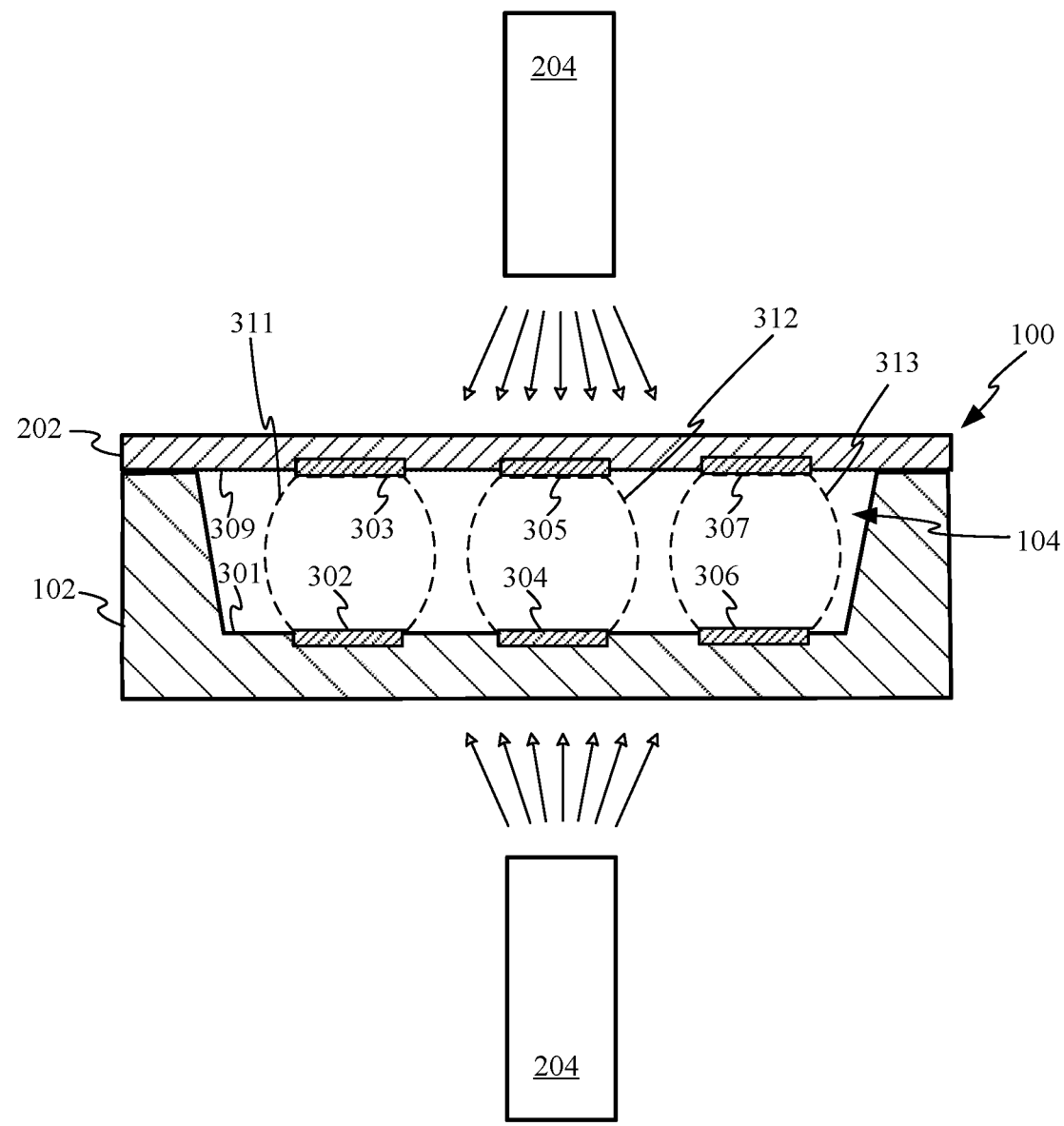
FIG. 3E shows a cross-sectional side view of an example reaction vessel with discrete regions on opposing interior-facing surfaces defining at least a portion of the reaction chamber.

FIG. 3E shows a cross-sectional side view of an example reaction vessel 100 with discrete regions 302-307 on opposing interior-facing surfaces 301 and 309 (e.g., of the top housing component 202 and the bottom housing component 102) defining at least a portion of the reaction chamber 104. In the illustrated example, the discrete regions 302-307 receive energy from the energy sources 204, causing the discrete regions 302-307 to be heated, and thereby increasing temperature of solution disposed within the reaction chamber 104. As illustrated, the discrete regions 302-307 may be plated or otherwise formed or deposited onto the interior-facing surfaces 301 and 309. Alternatively, in some embodiments, the discrete regions 302-307 may be disposed within or exterior to housing components (e.g., the top housing component 202 and the bottom housing component 102). In some embodiments, referencing FIG. 3E, while heat may diffuse over time across the entire reaction chamber 104, this diffusion is sufficiently slow such that there are periods where portions of the solution adjacent to the discrete regions 302-307 (e.g., within the heated areas 311, 312 and 313) may be heated to a higher temperature than the surrounding solution). In some embodiments, these portions may be cylindrical, concave cylindrical, convex cylindrical, spherical, etc. In some embodiments, the temperature gradient between the heated areas (e.g., the heated areas 311, 312 and 313) and the surrounding areas may result in thermal confinement of the molecules within the heated areas. For example, even though there may not be a physical barrier between the heated areas 311, 312, and 313, temperature differences may inhibit the diffusion of molecules from these areas to the surrounding solution, such that it may be said that the molecules within each of the heated areas are thermally confined within their respective areas. In this way, the heated areas 311, 312, and 313 may form sub-chambers that may be used to perform different reactions. In some embodiments, this thermal confinement may be caused by heating the discrete regions of the top housing component 202 and the bottom housing component 102 to at least threshold temperatures, which may be predetermined temperatures known to cause thermal confinement within the reaction vessel 100. For example, the discrete region 303 may be heated to a first threshold temperature, and the discrete region 302 may be heated to a second threshold temperature. In some cases, the first and second threshold temperature may be the same or substantially the same. In other cases, the first and second threshold temperatures may be different.

Figure 4A:
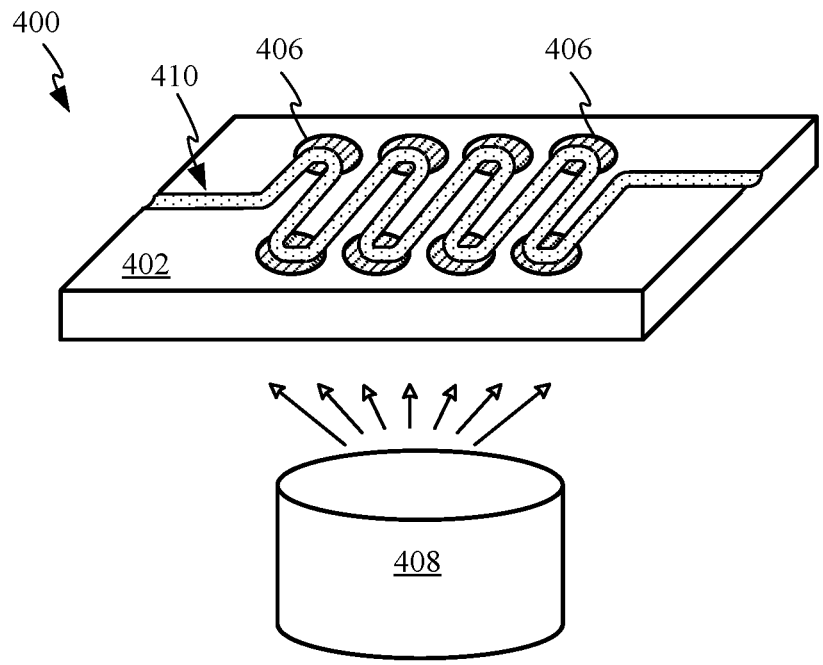
FIG. 4A shows a schematic perspective view of an example reaction vessel having a reaction chamber taking the form of a serpentine channel.

FIG. 4A shows a schematic perspective view of an example reaction vessel 400 that includes housing component 402. Housing component 402 includes a light absorbing layer distributed into multiple discrete regions 406 configured to receive optical radiation from energy source 408 for the localized heating of solution disposed within reaction vessel 400. In some embodiments, the light absorbing layer may be a contiguous, non-discrete layer with all portions obscured by the housing component 402 except for portions corresponding to the discrete regions 406. In other embodiments, the light absorbing layer may be discrete portions corresponding to the discrete regions 406 imposed on or within the housing component 402. As illustrated, housing component 402 may have a reaction chamber taking the form of a serpentine channel through which solution can flow through each of discrete regions 406. The flow of solution through serpentine channel 410 can be facilitated in many ways including by a pump, by gravity or by a wicking structure. It should be appreciated that each of discrete regions 406 can also be configured with its own respective energy source 408 similar to the configuration depicted in FIG. 3B.

Figure 4B:
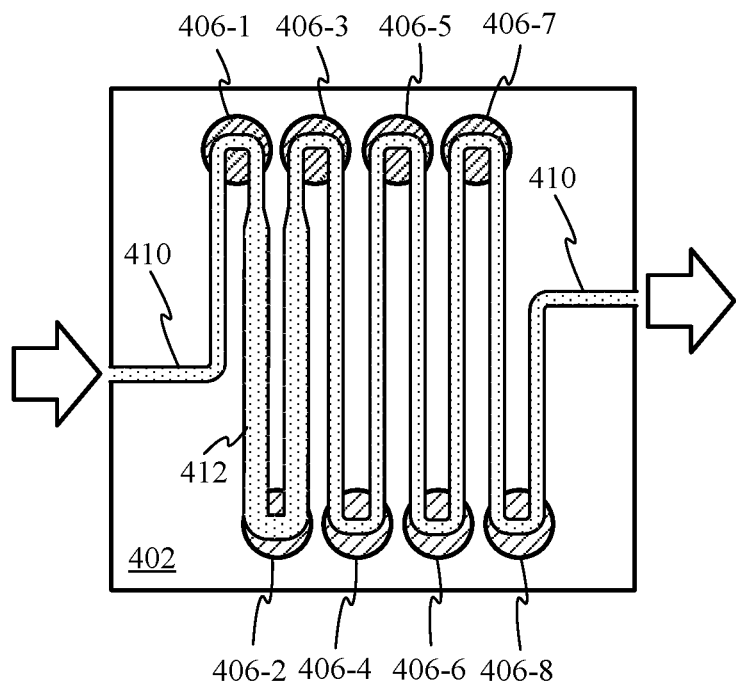
FIG. 4B shows a top view of the example reaction vessel depicted in FIG. 4A.

FIG. 4B shows a top view of an example reaction vessel 400 with a number of discrete regions 406-1 through 406-8 forming a light absorbing layer. While FIG. 4B shows a direction of the flow of solution through serpentine channel 410 in a first direction, it should be appreciated that the flow of solution through serpentine channel 410 can move in a second direction opposite the first direction. For example, in embodiments that include a pump mechanism, the flow of solution through serpentine channel 410 can be reversed at various points during a reaction to achieve a desired thermal heating profile for the solution disposed within channel 410. In some embodiments, single-stranded DNA can be affixed to a binder positioned atop one or more of discrete regions 406-1 through 406-8 allowing biological materials within the solution being conducted along channel 410 to interact with the single-stranded DNA at various temperatures generated by heat transferred to the solution at discrete regions 406-1 through 406-8. In some embodiments, heat absorbed by the discrete regions 406-1 through 406-8 may be varied by any of the mechanisms disclosed herein (e.g., by varying the composition of the discrete region, thickness of the discrete region, power level of corresponding light sources, position of corresponding light sources, etc.). In some embodiments, a speed at which the solution passes through portions of channel 410 can be varied by increasing the width and/or depth of the channel. By increasing the width and/or depth of a portion of a channel, the cross-sectional area A of the channel along that portion is increased. Thus, all else equal, the speed of the flow through that portion is decreased. For example, solution may flow more quickly through a portion of the channel having a relatively small average cross-sectional area as compared to a portion of the channel having a relatively large average cross-sectional area. According to the continuity equation for an incompressible fluid (which approximately applies for most solutions) $A_1v_1=A_2v_2$, when a cross-sectional area increases from a relatively low $A_1$ to a relatively high $A_2$, the speed must decrease to compensate (i.e., $v_1$ to $v_2$). For example, referencing FIG. 4B, channel segment 412 has an increased width, thereby reducing the speed and increasing the time the solution has to cool between discrete regions 406-1 and 406-2 (and between discrete regions 406-2 and 406-3), and further increasing the time the solution spends in discrete region 406-2. Adjusting the heat absorbed by the discrete regions 406-1 through 406-8, and/or adjusting the time a solution spends on each of the discrete regions 406-1 through 406-8 and in between the discrete regions 406-1 through 406-8 may allow for tailored multistep reactions. For example, as described below, PCR requires multiple steps, each step specifying a required temperature range (requiring heating and cooling) for a solution and further specifying an amount of time for which the solution is to remain at the required temperature range.

Figure 4C:
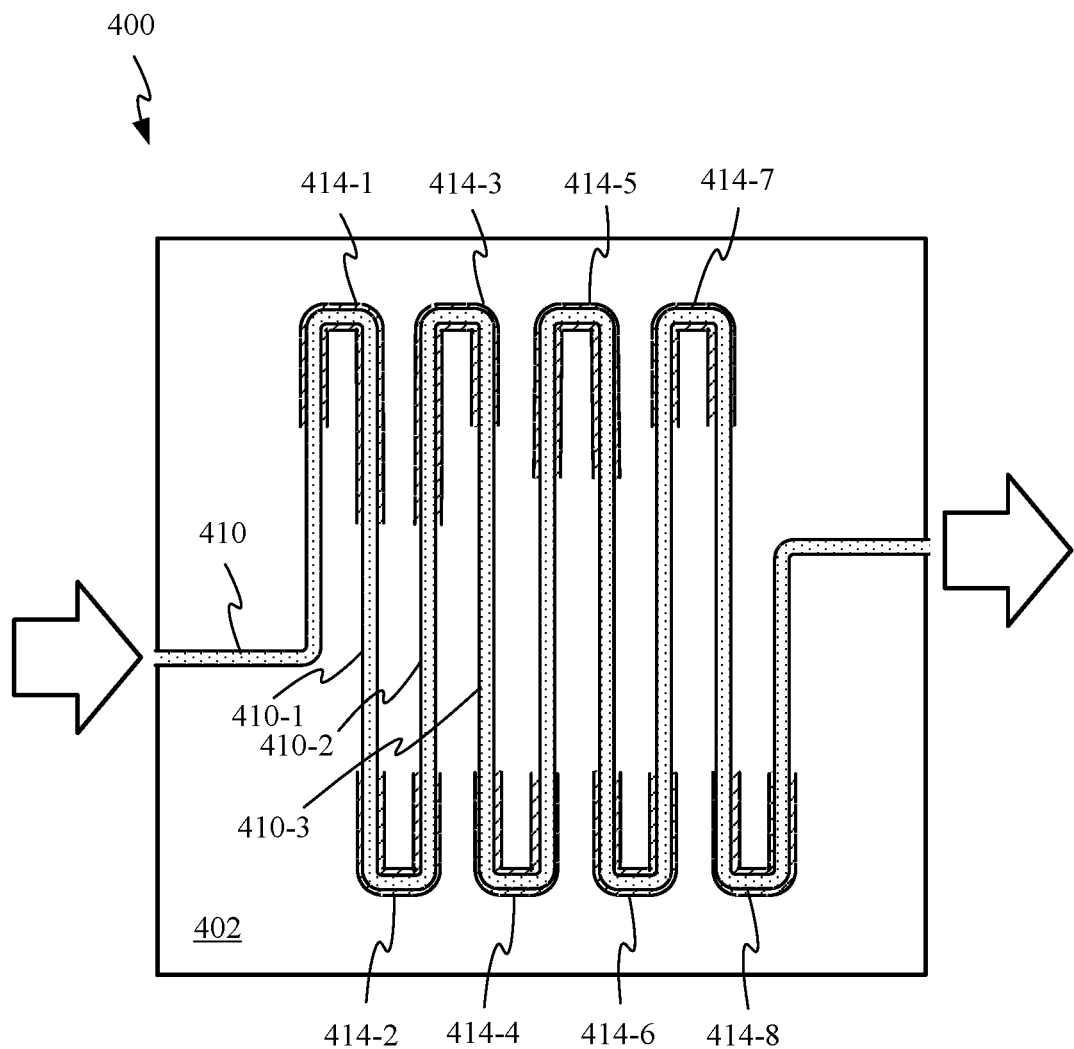
FIG. 4C shows another embodiment of an example reaction vessel that includes a light absorbing layer with conformal discrete regions.

FIG. 4C shows another embodiment of an example reaction vessel 400 that includes a light absorbing layer with conformal discrete regions 414. As illustrated in FIG. 4C, the conformal discrete regions 414 generally conform to the shape of segments of the channel 410. Conformal discrete regions allow the energy from an energy source to be targeted at specific segments of channel 410. In such embodiments, lengths of segments of channel 410 between sequential discrete regions can be increased or decreased (and similarly, lengths of segments of channel 410 associated with conformal discrete regions 414 can be increased or decreased). For example, solution flowing through segment 410-1 (the segment of channel 410 disposed between discrete regions 414-1 and 414-2) or segment 410-2 (the segment of channel 410 disposed between discrete regions 414-2 and 414-3) has less time to cool than when the solution is passing through segment 410-3 (the segment of channel 410 disposed between discrete regions 414-3 and region 414-4). This may be due to the fact that, as depicted, segments 410-1 and 410-2 are shorter than segment 410-3, and therefore have less opportunity to cool during their flow through the channel 410 between the heated discrete regions. As another example, the solution is heated for a longer time when it flows along region 414-1 than when it flows along region 414-2 (e.g., because, as depicted, the discrete region 414-1 is longer than the discrete region 414-2). As previously described, discrete regions of the embodiment illustrated in FIG. 4C may be modified to alter their respective temperature profiles (e.g., by varying their compositions, their thickness and other dimensions, etc.) or may receive different amounts of energy from one or more energy sources (e.g., by setting corresponding energy sources at different levels). Also as previously described, the channel 410 of the embodiment illustrated in FIG. 4C may be modified to alter flow (e.g., by varying the cross-sectional area A of the channel). Also as previously described, each of discrete regions 414 could be supported by a shared energy source, by its own dedicated energy source, or by an energy source that illuminates a subset of discrete regions 414. It should be appreciated that while reaction chambers have been described in the context of a unitary chamber as shown in FIGS. 1A-3B, a divided reaction chamber as shown in FIG. 3C and as a channel in FIGS. 4A-4C that other reaction chamber configurations are possible. For example, a reaction chamber could take the form of an interior volume defined by a series of glue channels positioned between two flat plates or could simply consist of a location on a reaction vessel substrate. In general, the reaction chamber can be considered to be any fluidic path defined by the reaction vessel along which various reactions can be initiated. The fluidic path could be closed/sealed or open to the environment in certain embodiments.

Figure 4D:
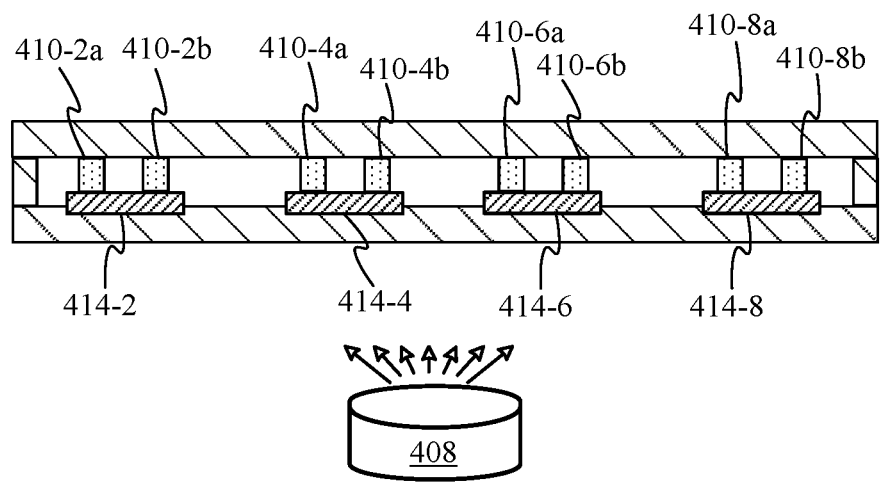
FIGS. 4D-4F show lateral cross sections of example reaction vessels such as the one shown in FIG. 4C.
Figure 4E:
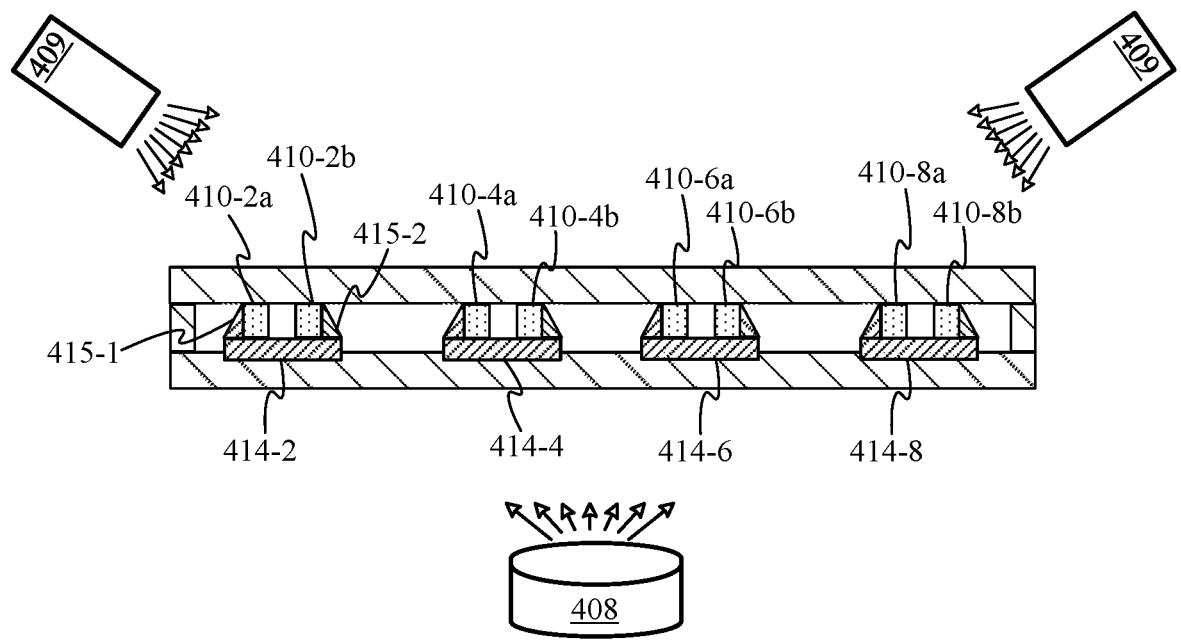
Figure 4F:
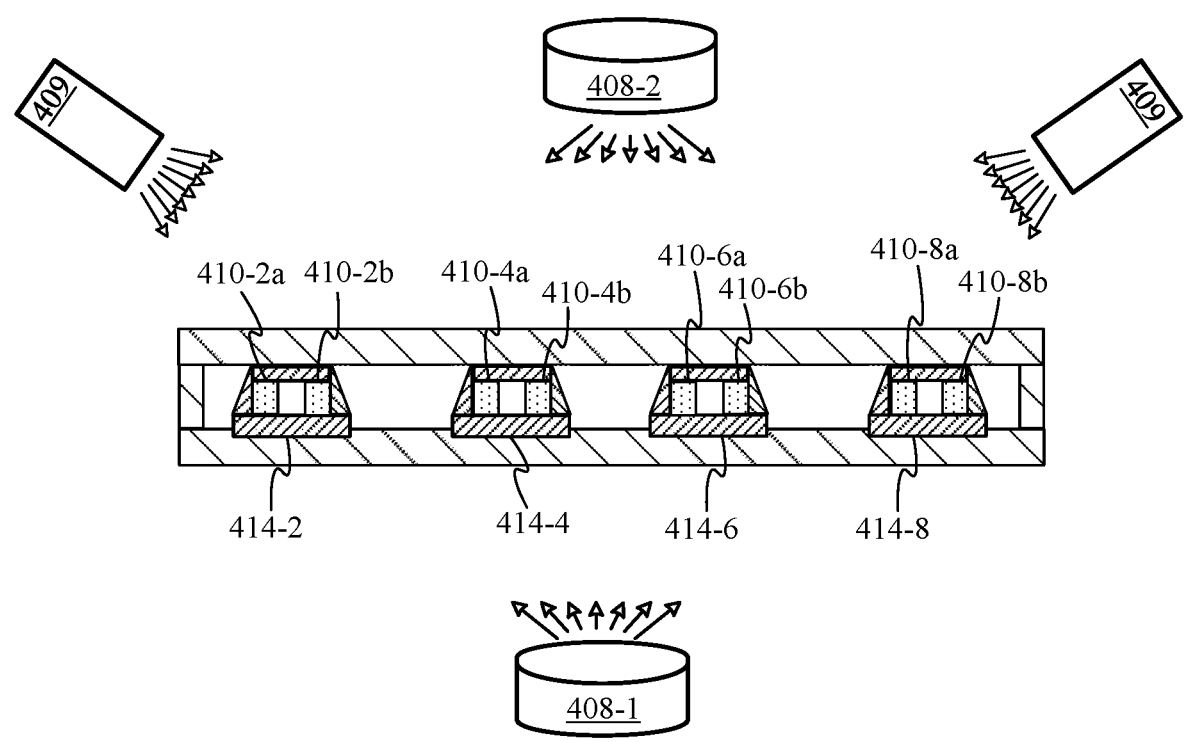

FIGS. 4D-4F show lateral cross sections of example reaction vessels such as the one shown in FIG. 4C. FIG. 4D shows a first example where discrete regions 414-2, 414-4, 414-6, and 414-8 are disposed beneath segments of channel 410 (e.g., segments 410-2*a*, 410-2*b*, 410-4*a*, 410-4*b*, 410-6*a*, 410-6*b*, 410-8*a*, 410-8*b*). As illustrated, the energy source 408 may direct energy toward the discrete regions so as to heat the solution within corresponding segments (e.g., segments directly above the discrete regions) of the channel 410. FIG. 4E shows a second example where discrete regions 414-2, 414-4, 414-6, and 414-8 include lateral portions (e.g., the lateral portions 415-1, 415-2) that heat lateral sides of the channel 410. As illustrated, in some embodiments, the lateral portions may have sloped ramps that are configured to receive light from the tilted energy sources 409. In the illustrated embodiments, the lateral portions are disposed along outer portions of the segments of channel 410 for each discrete region. For example, as illustrated, the lateral portion 415-1 is disposed along the outer lateral surface of the segment 410-2*a* and the lateral portion 415-2 is disposed along the outer lateral surface of the segment 410-2*b*. In other embodiments, the lateral portions may be disposed along both lateral services of each segment of channel 410. For example, lateral portions may be disposed along both lateral services of segment 410-2*a*. FIG. 4F shows a third example where discrete regions 414-2, 414-4, 414-6, and 414-8 further include top portions that overlay the segments of channel 410. In this illustrated example, the bottom portions of the discrete regions are configured to receive light from the energy source 408-1, the top portions of the discrete regions are configured to receive light from the energy source 408-2, and the lateral portions of the discrete regions are configured to receive light from the energy sources 409. As disclosed elsewhere herein, the energy absorbed by each of the discrete regions may be varied by, for example, by having a number of energy sources with variable power levels, varying the dimensions or compositions of the discrete regions, or any other suitable means.

Figure 5A:
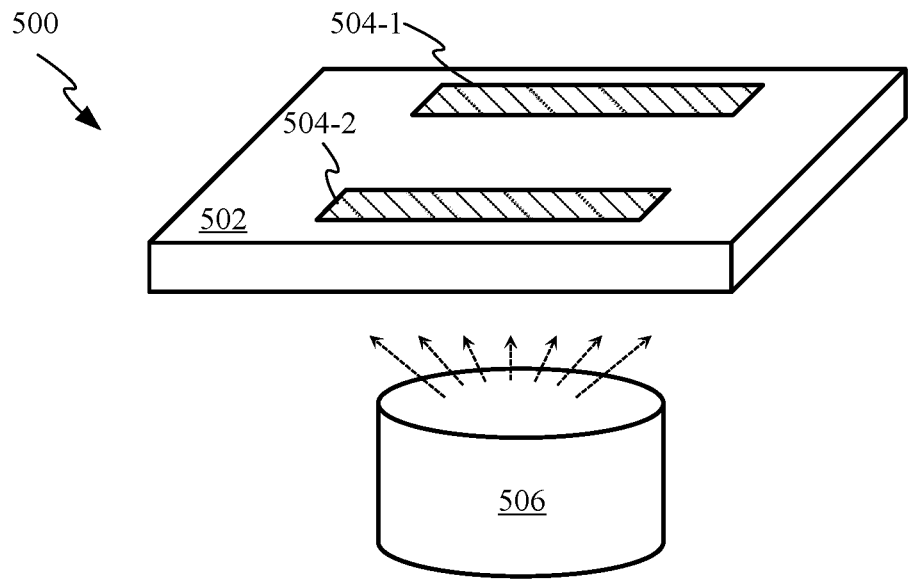
FIG. 5A shows an example reaction vessel that includes a housing component having a light absorbing layer made up of two discrete regions.
Figure 5B:
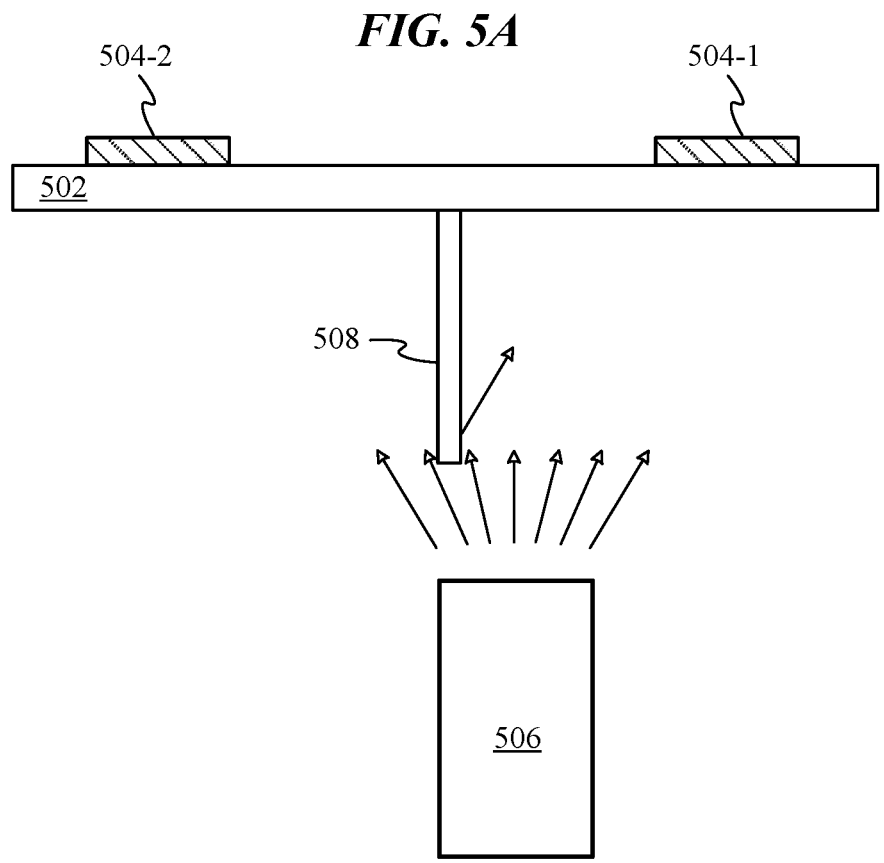
FIG. 5B shows how an energy source can be offset toward one of the two discrete regions such that one of the discrete regions receives more energy from the energy source than the other discrete region.

FIG. 5A shows an example reaction vessel 500 that includes a housing component 502 having a light absorbing layer made up of two discrete regions 504-1 and 504-2. In some embodiments, discrete regions 504-1 and 504-2 can be driven by a single energy source 506, allowing each of the discrete regions 504-1 and 504-2 to receive similar amounts of energy. In other embodiments, multiple energy sources may be used, as described elsewhere herein. FIG. 5B shows how energy source 506 can be offset toward discrete region 504-1 such that discrete region 504-1 receives more energy from energy source 506 than discrete region 504-2. This variance in energy between discrete regions 504-1 and 504-2 can be increased more by an optional reflector element 508 that further limits the amount of light arriving at discrete region 504-2 and is able to increase the light arriving at discrete region 504-1 by reflecting a portion of the light emitted by energy source 506 toward discrete region 504-1 as depicted. In some embodiments, the position of the reflector element 508 may be varied for a similar effect. For example, the energy source 506 may be positioned at a midpoint between discrete regions 504-1 and 504-2, but the reflector element 508 may be positioned closer to discrete region 504-2 such that a larger portion of light from the energy source 506 is blocked from discrete region 504-2 (e.g., and instead reflected toward discrete region 504-1). In some embodiments, reflector element 508 can be tilted to vary the distribution of light energy from energy source 506. For example, reflector element 508 may be tilted toward discrete element 504-1 to further increase the amount of light received from energy source 506.

Figure 5C:
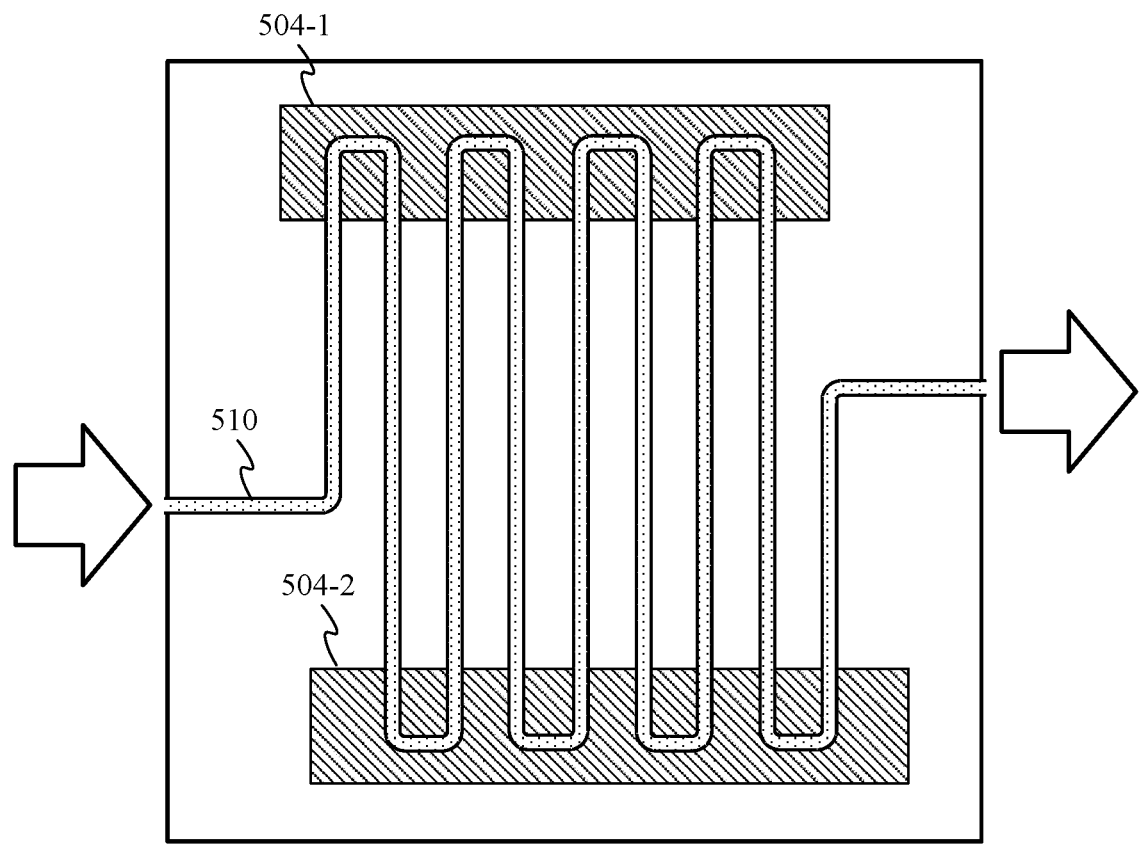
FIG. 5C shows a top view of the example reaction vessel depicted in FIGS. 5A and 5B and how the example reaction vessel can include a channel for guiding a solution back and forth between the two discrete regions.

FIG. 5C shows a top view of an example reaction vessel 500 and how it can include a channel 510 for guiding solution back and forth between discrete regions 504-1 and 504-2. In some embodiments, discrete regions 504-1 and 504-2 can receive the same amount of energy such that they are both at the same temperature. In this type of heating configuration, referencing FIG. 5C, solution flowing through channel 510 passes from discrete region 504-1 at time $T_1$, through a portion of channel 510 disposed between discrete regions 504-1 and 504-2 at time $T_2$ and then through discrete region 504-2 at time $T_3$. In this way the solution carried by channel 510 cycles from a first temperature at time $T_1$ to a second temperature at time $T_2$ and then back to the first temperature at time $T_3$. In other embodiments, discrete regions 504-1 and 504-2 can receive different amounts of energy by offsetting an associated energy source toward one of the discrete regions 504, by including dedicated energy sources for each of the discrete regions 504, by increasing or decreasing a thickness of a portion of the light absorbing layer making up one of the discrete regions 504, by varying the compositions of the light absorbing layers, etc. By configuring the system to provide different amounts of energy at discrete regions 504-1 and 504-2, solution flowing through channel 510 is able to reach a larger variety of temperatures as it flows from one end of channel 510 to another. Although the illustrated embodiment in FIG. 5C depicts only two discrete regions 504-1 and 504-2, this disclosure contemplates a similar embodiment having any number of discrete regions (e.g., a third discrete region set to a third temperature disposed in between the discrete regions 504-1 and 504-2). The described heating model may be particularly suited for multistep reactions (e.g., for PCR).

Exemplary PCR Reactions

PCR amplifies a specific region of a DNA strand (the DNA target). Most PCR methods amplify DNA fragments of between 0.1 and 10 kilo basepairs (kb). The amount of amplified product is determined by the available substrates in the reaction, which become limiting as the reaction progresses. A basic PCR set-up requires several components and reagents, including: a DNA template that contains the DNA target region to amplify; a DNA polymerase, an enzyme that polymerizes new DNA strands; heat-resistant Taq polymerase is especially common, as it is more likely to remain intact during the high-temperature DNA denaturation process; two DNA primers that are complementary to the 3' ends of each of the sense and anti-sense strands of the DNA target; specific primers that are complementary to the DNA target region are selected beforehand, and are often custom-made in a laboratory or purchased from commercial biochemical suppliers; deoxynucleoside triphosphates, or dNTPs; a buffer solution providing a suitable chemical environment for optimum activity and stability of the DNA polymerase; bivalent cations, typically magnesium (Mg) or manganese (Mn) ions; Mg2+ is the most common, but Mn2+ can be used for PCR-mediated DNA mutagenesis, as a higher Mn2+ concentration increases the error rate during DNA synthesis; and monovalent cations, typically potassium (K) ions.

The reaction is commonly carried out in a volume of 10-200 μl in small reaction chambers (0.2-0.5 ml volumes) in a thermal cycler, which heats and cools the reaction tubes to achieve the temperatures required at each step of the reaction. Thin-walled reaction tubes permit favorable thermal conductivity to allow for rapid thermal equilibration.

Figure 6:
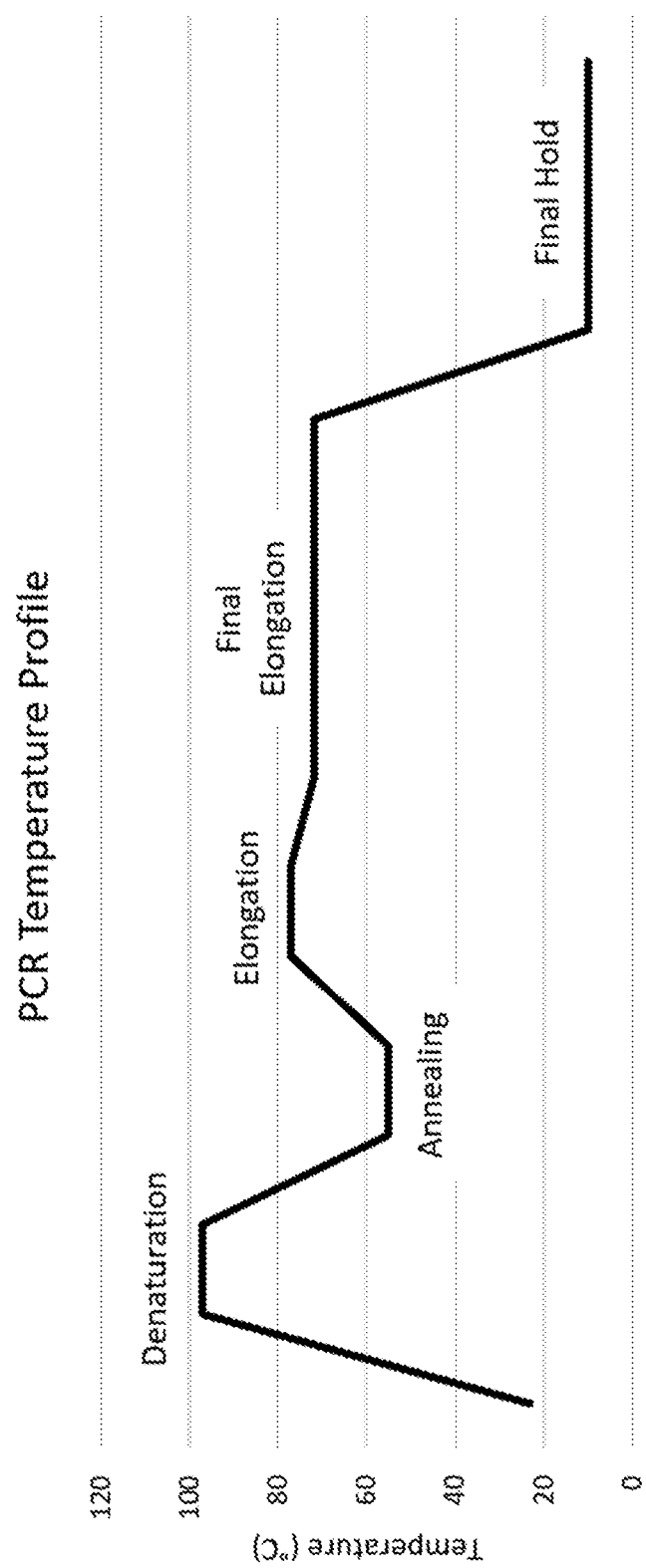
FIG. 6 illustrates an example temperature profile of a reaction vessel, distinctly showing various steps associated with a single PCR cycle.

FIG. 6 illustrates an example temperature profile of a reaction vessel, distinctly showing various steps associated with a single PCR cycle. Typically, PCR consists of a series of 20-40 repeated temperature changes, called cycles, with each cycle commonly consisting of two or three discrete temperature steps. The cycling is often preceded by a single temperature step at a very high temperature (>90° C. [194° F.]), followed by one hold at the end for final product extension or brief storage. The temperatures used and the length of time they are applied in each cycle depend on a variety of parameters, including the enzyme used for DNA synthesis, the concentration of bivalent ions and dNTPs in the reaction, and the melting temperature (Tm) of the primers. The individual steps common to most PCR methods are as follows:

(1) Initialization: This step is only required for DNA polymerases that require heat activation by hot-start PCR. It consists of heating the reaction chamber to a temperature of 94-96° C. (201-205° F.), or 98° C. (208° F.) if extremely thermostable polymerases are used, which is then held for 1-10 minutes. This step is not illustrated in FIG. 6.

(2) Denaturation: This step is the first regular cycling event and consists of heating the reaction chamber to 94-98° C. (201-208° F.) for 20-30 seconds. This causes DNA melting, or denaturation, of the double-stranded DNA template by breaking the hydrogen bonds between complementary bases, yielding two single-stranded DNA molecules.

(3) Annealing: In the next step, the reaction temperature is lowered to 50-65° C. (122-149° F.) for 20-40 seconds, allowing annealing of the primers to each of the single-stranded DNA templates. Two different primers are typically included in the reaction mixture: one for each of the two single-stranded complements containing the target region. The primers are single-stranded sequences themselves, but are much shorter than the length of the target region, complementing only very short sequences at the 3' end of each strand. The correct temperature for the annealing step is important, since this temperature strongly affects efficiency and specificity. This temperature must be low enough to allow for hybridization of the primer to the strand, but high enough for the hybridization to be specific, i.e., the primer should bind only to a perfectly complementary part of the strand, and nowhere else. If the temperature is too low, the primer may bind imperfectly. If it is too high, the primer may not bind at all. A typical annealing temperature is about 3-5° C. below the Tm of the primers used. Stable hydrogen bonds between complementary bases are formed only when the primer sequence very closely matches the template sequence. During this step, the polymerase binds to the primer-template hybrid and begins DNA formation.

(4) Extension/elongation: The temperature at this step depends on the DNA polymerase used; the optimum activity temperature for the thermostable DNA polymerase of Taq (*Thermus aquaticus*) polymerase is approximately 75-80° C. (167-176° F.), though a temperature of 72° C. (162° F.) is commonly used with this enzyme. In this step, the DNA polymerase synthesizes a new DNA strand complementary to the DNA template strand by adding free dNTPs from the reaction mixture that are complementary to the template in the 5'-to-3' direction, condensing the 5'-phosphate group of the dNTPs with the 3'-hydroxy group at the end of the nascent (elongating) DNA strand. The precise time required for elongation depends both on the DNA polymerase used and on the length of the DNA target region to amplify. As a rule of thumb, at their optimal temperature, most DNA polymerases polymerize a thousand bases per minute. Under optimal conditions (i.e., if there are no limitations due to limiting substrates or reagents), at each extension/elongation step, the number of DNA target sequences is doubled. With each successive cycle, the original template strands plus all newly generated strands become template strands for the next round of elongation, leading to exponential (geometric) amplification of the specific DNA target region.

The processes of denaturation, annealing and elongation constitute a single cycle. Multiple cycles are required to amplify the DNA target to millions of copies. The formula used to calculate the number of DNA copies formed after a given number of cycles is 2n, where n is the number of cycles.

(5) Final elongation: This single step is optional, but is performed at a temperature of 70-74° C. (158-165° F.) (the temperature range required for optimal activity of most polymerases used in PCR) for 5-15 minutes after the last PCR cycle to ensure that any remaining single-stranded DNA is fully elongated.

(6) Final hold: The final step cools the reaction chamber to 4-15° C. (39-59° F.) for an indefinite time, and may be employed for short-term storage of the PCR products.

To check whether the PCR successfully generated the anticipated DNA target region (also sometimes referred to as the amplimer or amplicon), agarose gel electrophoresis may be employed for size separation of the PCR products. The size(s) of PCR products is determined by comparison with a DNA ladder, a molecular weight marker which contains DNA fragments of known size run on the gel alongside the PCR products. As with other chemical reactions, the reaction rate and efficiency of PCR are affected by limiting factors. Thus, the entire PCR process can further be divided into three stages based on reaction progress:

(1) Exponential amplification: At every cycle, the amount of product is doubled (assuming 100% reaction efficiency). After 30 cycles, a single copy of DNA can be increased up to one billion copies. The reaction is very sensitive: only minute quantities of DNA must be present.

(2) Leveling off stage: The reaction slows as the DNA polymerase loses activity and as consumption of reagents such as dNTPs and primers causes them to become limiting.

(3) Plateau: No more product accumulates due to exhaustion of reagents and enzyme.

Upon loading and sealing, the system may generate an amplified product through thermal cycling. Thermal cycling may comprise one or more cycles of incubating a reaction mixture at a denaturation temperature for a denaturation time period followed by incubating the mixture at an annealing temperature for an annealing time period further followed by incubating the mixture at an elongation temperature for an elongation time period. A system may heat the wells of the reaction well by using one or more light sources as previously described. Focused light by lens between light source and reaction well may be used also. The embedded lens may be used to focus emission from the fluorescent dye integrated in the reaction vessel/wells. For the cooling of the sample and reagents, the one or more light sources may be turned off for a cooling time period. In some cases, a fluid circulation channel may be used as previously described for the cooling of the reagents and samples in the wells of the reaction well.

Amplification of a sample may be performed by using the systems described previously to perform one or more thermal cycles comprising a denaturation cycle, an annealing cycle and an elongation cycle. The time in which an amplification reaction may yield a detectable result in the form of an amplified product may vary depending on the target nucleic acid, the sample, the reagents used and the protocol for PCR. In some cases, an amplification process may be performed in less than 1 minute. In some cases, an amplification process may be performed in about 1 minute to about 40 minutes. In some cases, an amplification process may be performed in at least about 1 minute. In some cases, an amplification process may be performed in at most about 40 minutes. In some cases, an amplification process may be performed in about 1 minute to about 5 minutes, about 1 minute to about 10 minutes, about 1 minute to about 15 minutes, about 1 minute to about 20 minutes, about 1 minute to about 25 minutes, about 1 minute to about 30 minutes, about 1 minute to about 35 minutes, about 1 minute to about 40 minutes, about 5 minutes to about 10 minutes, about 5 minutes to about 15 minutes, about 5 minutes to about 20 minutes, about 5 minutes to about 25 minutes, about 5 minutes to about 30 minutes, about 5 minutes to about 35 minutes, about 5 minutes to about 40 minutes, about 10 minutes to about 15 minutes, about 10 minutes to about 20 minutes, about 10 minutes to about 25 minutes, about 10 minutes to about 30 minutes, about 10 minutes to about 35 minutes, about 10 minutes to about 40 minutes, about 15 minutes to about 20 minutes, about 15 minutes to about 25 minutes, about 15 minutes to about 30 minutes, about 15 minutes to about 35 minutes, about 15 minutes to about 40 minutes, about 20 minutes to about 25 minutes, about 20 minutes to about 30 minutes, about 20 minutes to about 35 minutes, about 20 minutes to about 40 minutes, about 25 minutes to about 30 minutes, about 25 minutes to about 35 minutes, about 25 minutes to about 40 minutes, about 30 minutes to about 35 minutes, about 30 minutes to about 40 minutes, or about 35 minutes to about 40 minutes. In some cases, an amplification process may be performed in about 1 minute, about 5 minutes, about 10 minutes, about 15 minutes, about 20 minutes, about 25 minutes, about 30 minutes, about 35 minutes, or about 40 minutes.

In some cases, amplification of a sample may be performed by repeating the thermal cycle 5 to 40 times. In some cases, the thermal cycle may be repeated at least 5 times. In some cases, the thermal cycle may be repeated at most 60 times. In some cases, the thermal cycle may be repeated 5 times, 10 times, 15 times, 20 times, 25 times, 30 times, 35 times 40 times, 45 times, 50 times, 55 times or 60 times.

A thermal cycle may be completed in a thermal cycling time period. In some cases, a thermal cycling time period may range from 2 seconds to 60 seconds per cycle. In some cases, a thermal cycle may be completed in about 2 seconds to about 60 seconds. In some cases, a thermal cycle may be completed in at least about 2 seconds. In some cases, a thermal cycle may be completed in at most about 60 seconds. In some cases, a thermal cycle may be completed in about 2 seconds to about 5 seconds, about 2 seconds to about 10 seconds, about 2 seconds to about 20 seconds, about 2 seconds to about 40 seconds, about 2 seconds to about 60 seconds, about 5 seconds to about 10 seconds, about 5 seconds to about 20 seconds, about 5 seconds to about 40 seconds, about 5 seconds to about 60 seconds, about 10 seconds to about 20 seconds, about 10 seconds to about 40 seconds, about 10 seconds to about 60 seconds, about 20 seconds to about 40 seconds, about 20 seconds to about 60 seconds, or about 40 seconds to about 60 seconds. In some cases, a thermal cycle may be completed in about 2 seconds, about 5 seconds, about 10 seconds, about 20 seconds, about 40 seconds, or about 60 seconds.

The temperature and time period of the denaturation cycle may be dependent on the properties sample to be identified, the reagents and the amplification protocol being used. A denaturation cycle may be performed at temperatures ranging from about 80° C. to about 110° C. A denaturation cycle may be performed at a temperature of at least about 80° C. A denaturation cycle may be performed at a temperature of at most about 110° C. A denaturation cycle may be performed at a temperature of about 80° C. to about 85° C., about 80° C. to about 90° C., about 80° C. to about 95° C., about 80° C. to about 100° C., about 80° C. to about 105° C., about 80° C. to about 110° C., about 85° C. to about 90° C., about 85° C. to about 95° C., about 85° C. to about 100° C., about 85° C. to about 105° C., about 85° C. to about 110° C., about 90° C. to about 95° C., about 90° C. to about 100° C., about 90° C. to about 105° C., about 90° C. to about 110° C., about 95° C. to about 100° C., about 95° C. to about 105° C., about 95° C. to about 110° C., about 100° C. to about 105° C., about 100° C. to about 110° C., or about 105° C. to about 110° C. A denaturation cycle may be performed at a temperature of about 80° C., about 85° C., about 90° C., about 95° C., about 100° C., about 105° C., or about 110° C.

In some cases, the time period of a denaturation cycle may be less than about 1 second. In some cases, the time period of a denaturation cycle may be at most about 100 seconds. In some cases, the time period of a denaturation cycle may be about 0 second to 1 second, about 1 second to about 5 seconds, about 1 second to about 10 seconds, about 1 second to about 20 seconds, about 1 second to about 40 seconds, about 1 second to about 60 seconds, about 1 second to about 100 seconds, about 5 seconds to about 10 seconds, about 5 seconds to about 20 seconds, about 5 seconds to about 40 seconds, about 5 seconds to about 60 seconds, about 5 seconds to about 100 seconds, about 10 seconds to about 20 seconds, about 10 seconds to about 40 seconds, about 10 seconds to about 60 seconds, about 10 seconds to about 100 seconds, about 20 seconds to about 40 seconds, about 20 seconds to about 60 seconds, about 20 seconds to about 100 seconds, about 40 seconds to about 60 seconds, about 40 seconds to about 100 seconds, or about 60 seconds to about 100 seconds. In some cases, the time period of a denaturation cycle may be less than about 1 second, about 5 seconds, about 10 seconds, about 20 seconds, about 40 seconds, about 60 seconds, or about 100 seconds.

The temperature and time period of the annealing and elongation cycles may be dependent on the properties sample to be identified, the reagents and the amplification protocol being used. An annealing and/or elongation cycle may be performed at a temperature of about 40° C. to about 70° C. An annealing and/or elongation cycle may be performed at a temperature of at least about 40° C. An annealing and/or elongation cycle may be performed at a temperature of at most about 70° C. An annealing and/or elongation cycle may be performed at a temperature of about 40° C. to about 45° C., about 40° C. to about 50° C., about 40° C. to about 55° C., about 40° C. to about 60° C., about 40° C. to about 65° C., about 40° C. to about 70° C., about 45° C. to about 50° C., about 45° C. to about 55° C., about 45° C. to about 60° C., about 45° C. to about 65° C., about 45° C. to about 70° C., about 50° C. to about 55° C., about 50° C. to about 60° C., about 50° C. to about 65° C., about 50° C. to about 70° C., about 55° C. to about 60° C., about 55° C. to about 65° C., about 55° C. to about 70° C., about 60° C. to about 65° C., about 60° C. to about 70° C., or about 65° C. to about 70° C. An annealing and/or elongation cycle may be performed at a temperature of about 40° C., about 45° C., about 50° C., about 55° C., about 60° C., about 65° C., or about 70° C.

In some cases, the time period of an annealing and/or elongation cycle may be less than about 1 second. In some cases, the time period of an annealing and/or elongation cycle may be at most about 60 seconds. In some cases, the time period of an annealing and/or elongation cycle may be about 0 seconds to 1 seconds, about 1 second to about 5 seconds, about 1 second to about 10 seconds, about 1 second to about 20 seconds, about 1 second to about 40 seconds, about 1 second to about 60 seconds, about 5 seconds to about 10 seconds, about 5 seconds to about 20 seconds, about 5 seconds to about 40 seconds, about 5 seconds to about 60 seconds, about 10 seconds to about 20 seconds, about 10 seconds to about 40 seconds, about 10 seconds to about 60 seconds, about 20 seconds to about 40 seconds, about 20 seconds to about 60 seconds, or about 40 seconds to about 60 seconds. In some cases, the time period of an annealing and/or elongation cycle may be less than about 1 second, about 5 seconds, about 10 seconds, about 20 seconds, about 40 seconds, or about 60 seconds.

In some cases, a cooling cycle may be performed between the denaturation cycle and annealing and/or elongation cycles. In some cases, a cooling cycle may be performed for about 1 second to about 60 seconds. In some cases, a cooling cycle may be performed for at least about 1 second. In some cases, a cooling cycle may be performed for at most about 60 seconds. In some cases, a cooling cycle may be performed for about 1 second to about 5 seconds, about 1 second to about 10 seconds, about 1 second to about 20 seconds, about 1 second to about 30 seconds, about 1 second to about 40 seconds, about 1 second to about 50 seconds, about 1 second to about 60 seconds, about 5 seconds to about 10 seconds, about 5 seconds to about 20 seconds, about 5 seconds to about 30 seconds, about 5 seconds to about 40 seconds, about 5 seconds to about 50 seconds, about 5 seconds to about 60 seconds, about 10 seconds to about 20 seconds, about 10 seconds to about 30 seconds, about 10 seconds to about 40 seconds, about 10 seconds to about 50 seconds, about 10 seconds to about 60 seconds, about 20 seconds to about 30 seconds, about 20 seconds to about 40 seconds, about 20 seconds to about 50 seconds, about 20 seconds to about 60 seconds, about 30 seconds to about 40 seconds, about 30 seconds to about 50 seconds, about 30 seconds to about 60 seconds, about 40 seconds to about 50 seconds, about 40 seconds to about 60 seconds, or about 50 seconds to about 60 seconds. In some cases, a cooling cycle may be performed for about 1 second, about 5 seconds, about 10 seconds, about 20 seconds, about 30 seconds, about 40 seconds, about 50 seconds, or about 60 seconds.

Detection of the amplified product may be performed at various stages of the amplification process. In some cases, the detection of an amplified product may be performed at the end of the amplification process. In some cases, the detection of the amplified product may be performed during a thermal cycle. Alternatively, in some cases, detection may be performed at the end of each thermal cycle. In addition to the detection methods described herein, detection of an amplified product may be performed using gel electrophoresis, capillary electrophoresis, sequencing, short tandem repeat analysis and other known methods.

Figure 7A:
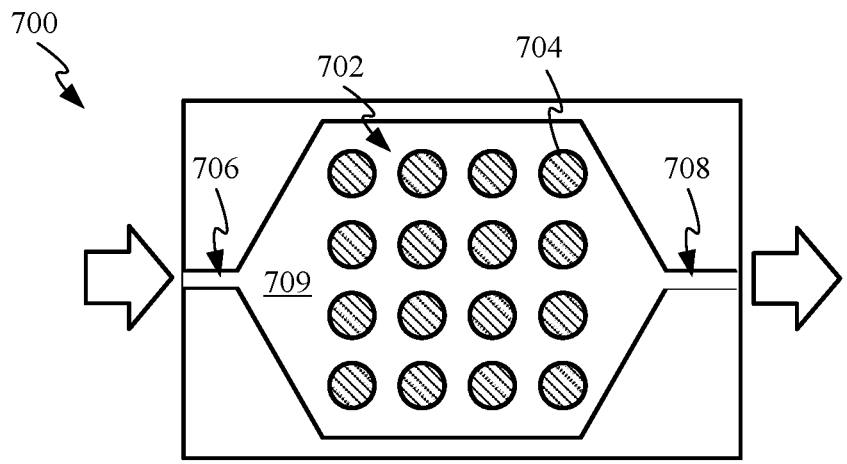
FIGS. 7A-7C show examples of hybridization and solid-phase PCR operations in a reaction vessel having a light absorbing layer with multiple discrete regions.
Figure 7B:
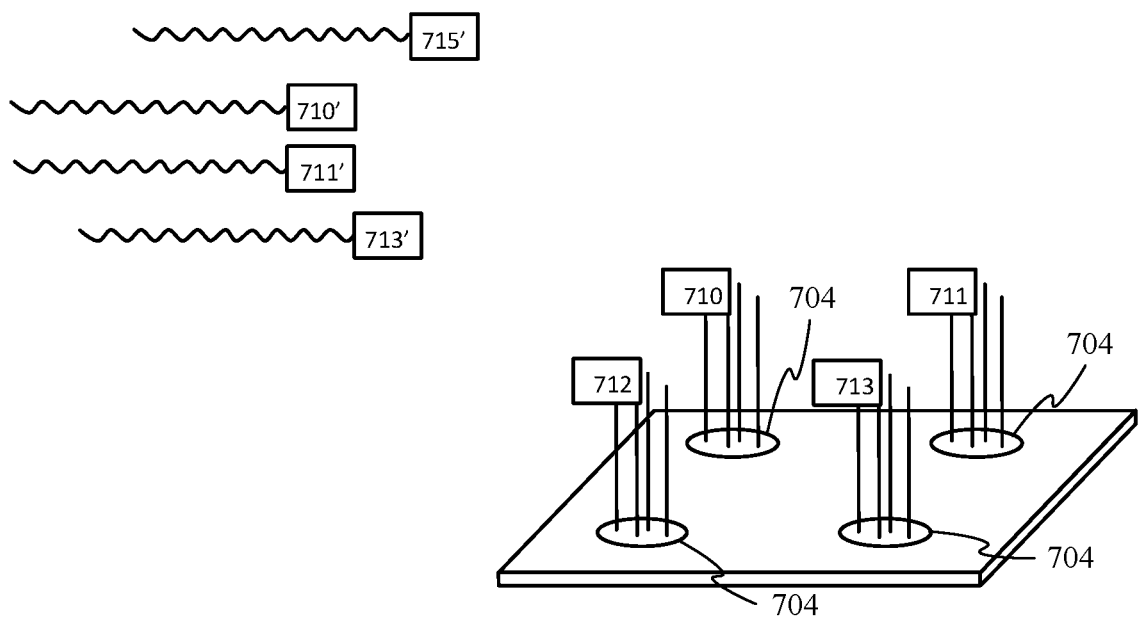
Figure 7C:
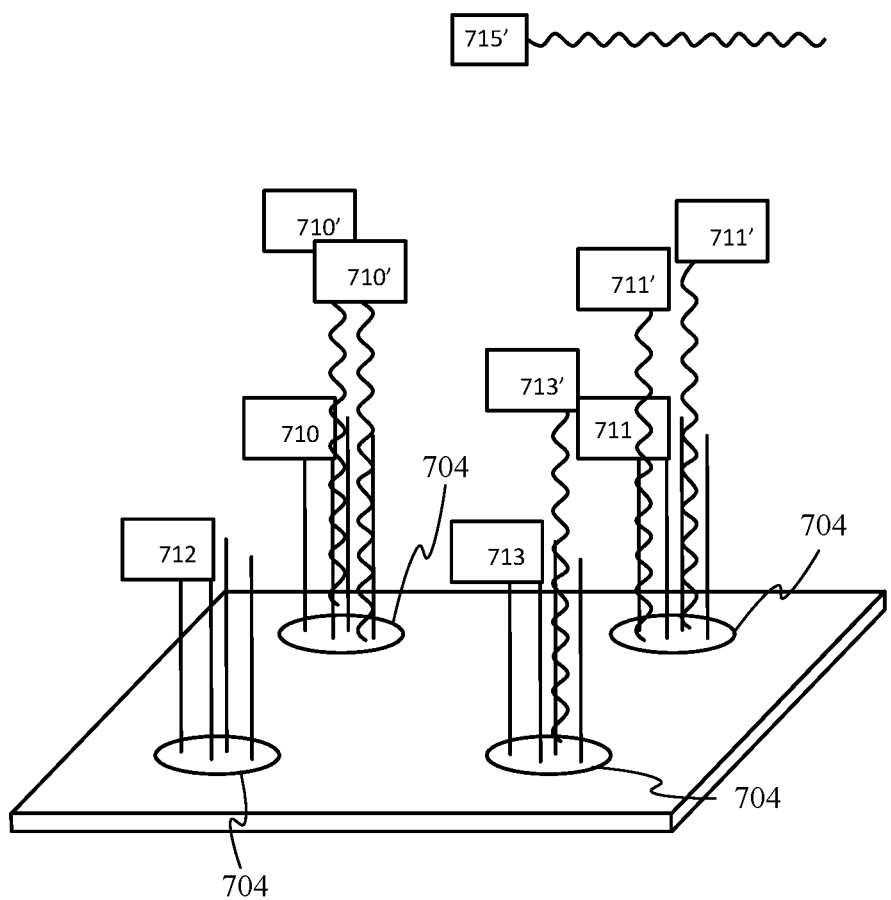

FIGS. 7A-7C show examples of hybridization and solid-phase PCR operations in a reaction vessel 700 having a light absorbing layer with multiple discrete regions. FIG. 7A shows a top view of a reaction vessel 700 having a light absorbing layer 702 that includes an array of discrete regions 704 arranged in a grid pattern. Reaction vessel 700 includes inlet port 706 and an outlet port 708 that are configured to allow solution to flow into and out of reaction chamber 709. In some embodiments, the reaction chamber 709 may not include any physical barriers that separate the different discrete regions 704. Instead, referencing the example embodiment in FIG. 7A, a solution may be made to flow into the reaction vessel 700 via the inlet port 706 and over the interior surfaces of the reaction chamber 709 so that the solution contacts the various discrete regions 704. The solution may exit the reaction vessel 700 via the outlet port 708. Such embodiments, where the reaction chambers 709 are not required to be separated by physical barriers, may be advantageous in that they are relatively less complicated and more cost-effective when compared to reaction vessels with physically separated reaction chambers 709. The simplicity afforded by a reaction vessel with a single chamber that is not separated by physical barriers may translate to fewer malfunctions and/or defects, as well as reduced labor and cost requirements for manufacturing and assembly. In other embodiments, one or more of the discrete regions 704 may be separated from one or more other discrete regions 704 by a physical barrier (e.g., by one or more protrusions extending from the top and/or bottom housing components, or by any other suitable mechanism such as those disclosed elsewhere herein), such that there may be more than one reaction chamber within the reaction vessel 700. In some embodiments, the reaction chamber 709 may include discrete regions on opposing sides (e.g., formed or deposited along a top interior-facing surface and along a bottom interior-facing surface). In some of these embodiments, the concept of thermal confinement (as described elsewhere herein) may be used to separate portions of solution from each other. In some embodiments, the surface area of the binding region associated with the discrete regions 704 may be varied. For example, a first discrete region 704 may have a smaller surface area than a second discrete region 704. As a result, the temperature profile of the first discrete region 704 may be different from the temperature profile of the second discrete region 704. Additionally, the second discrete region 704, by virtue of having a larger surface area, may bind a larger number of sequences than the first discrete region 704, which may be used, for example, to skew an amplification process in favor of the sequences bound to the second discrete region 704. In some embodiments, as disclosed elsewhere herein, the temperature profile of a discrete region 704 may be further varied by varying an amount of light energy delivered to the discrete region 704 (e.g., by modulating energy levels of energy sources corresponding to the discrete region 704), and/or an amount of light energy absorbed by the discrete region 704 (e.g., by adjusting properties such as composition and thickness of the discrete region 704).

In some embodiments, one or more of the discrete elements of a reaction vessel may be bound to one or more nucleotide sequences. For example, referencing the example illustrated in FIG. 7B, each discrete element 704 possesses a unique probe or primer sequence 710-713 bound, for example, by weak covalent interactions (e.g., Au-thiol). as illustrated, a solution including the target molecules 710', 711' and 713' may be flowed over the discrete regions 704. The target molecules 710', 711' and 713' may be sequences that are complementary to sequences bound to the discrete regions 704 (i.e., the sequences 710, 711 and 713), but the target molecule 715' may not be complementary to the sequences bound to the discrete regions 704. In some embodiments, target molecules 710', 711', 713' and 715' can be labeled for detection purposes.

In some embodiments, as the solution is caused to flow across the discrete regions 704, target molecules in the solution that are complementary to sequences bound to the discrete regions 704 may hybridize with those sequences. FIG. 7C shows how target molecules only hybridize with their complementary sequence bound on the surface. For example, as illustrated in FIG. 7C, target molecules 710', 711' and 713' hybridize with their respective complementary sequences 710, 711 and 713 that are themselves bound to their respective discrete regions 704. Thus, target molecules 710', 711' and 713' become bound to the discrete regions 704 via their respective complementary sequences. Target molecules that do not have complementary sequences (e.g., the target molecule 715') may not hybridize, and may therefore be left unbound in solution. These unbound molecules may leave the reaction vessel when the solution is caused to flow out of the reaction vessel (e.g., referencing vague 7A, via the outlet port 708). Similarly, sequences bound to discrete regions 704 that do not have complementary target molecules in solution do not hybridize. For example, as illustrated in FIG. 7C, the sequences 712 remain un-hybridized. As mentioned previously, in some embodiments, the target molecules may be labeled for detection purposes. For example, the target molecules may be fluorescently labeled. Once a solution has been flowed into and out of the reaction vessel (after sufficient time has been allowed for hybridization), a detection mechanism may be used to detect the presence of target molecules that have been labeled. For example, the detection mechanism may include a light source designed to excite fluorescent labels bound to target molecules and a camera device for detecting the presence of the fluorescent labels. In this example, the florescent light source may be shined on the reaction vessel, and the resulting fluorescence intensity at each discrete region can be used to detect the presence or absence of a given target molecule. For example, referencing FIG. 7C, shining a suitable light source at the discrete regions 704 after the solution has been allowed to leave the reaction vessel (along with unbound target molecules such as the target molecule 715') may cause the fluorescent labels of all bound target molecules to fluoresce. A camera may detect that areas corresponding to discrete regions 704 associated with the sequences 710, 711 and 713 fluoresce above a threshold intensity, while the area corresponding to the discrete region 704 associated with the sequence 712 does not fluoresce above the threshold intensity (because it lacks target molecules with fluorescent labels).

Following hybridization of the target molecules with the sequences bound to the discrete regions, solid-phase PCR can be performed to create a population of discrete amplicons, which can then be detected via a molecule that binds to DNA, and can be used to detect the presence of said molecule (e.g., through fluorescence and/or electrochemical signal). Solid-phase PCR uses surface-bound primers on the discrete regions instead of freely-diffusing primers to amplify DNA. This limits the nucleic acids amplification to two-dimensional surfaces on the discrete regions and therefore allows for easy parallelization and high multiplexing of DNA amplification and detection in a single reaction vessel system. Alternatively, amplicons can be sequenced to identify the presence of said molecule.

Figure 7D:
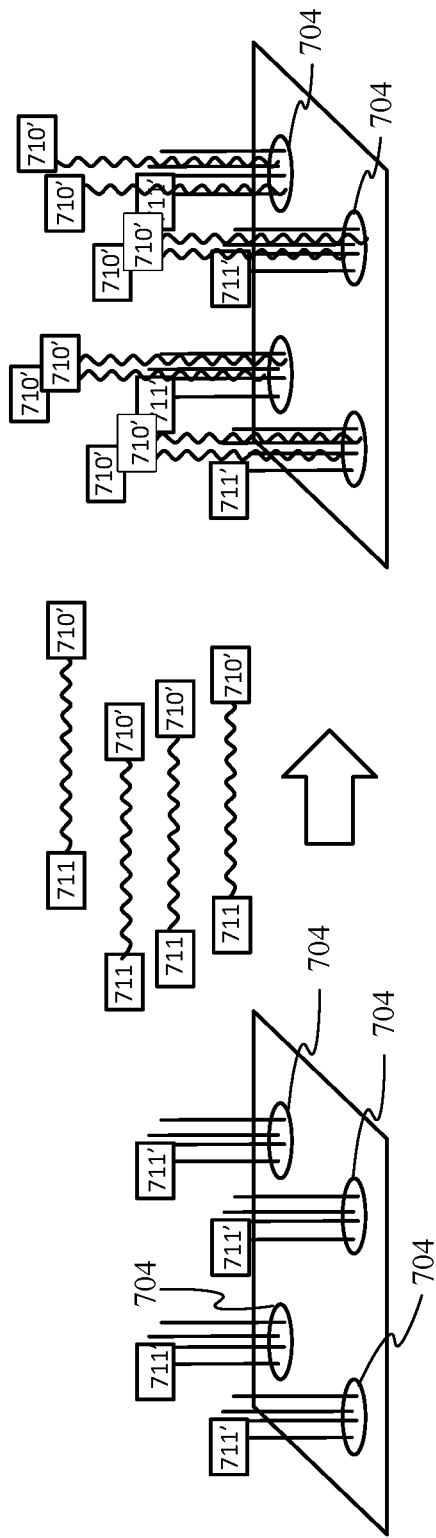
FIG. 7D shows another example of solid phase PCR in which single strands of DNA are bonded to single strand DNA attached to discrete regions of a light absorbing layer.

FIG. 7D shows another example where each discrete region 704 possesses a unique primer sequence 711' bound by weak covalent interactions (e.g., Au-thiol). As illustrated, a solution including target molecules 711, 710' may be caused to flow over the discrete regions 704. We target molecules 711, 710' may include an adaptor portion 711 that is complementary to the unique primer sequence 711' and a second portion (e.g., a portion of a DNA molecule or an RNA molecule). For example, the adapter portion 711 may be an adapter (configured to bind to the unique primer sequence 711') that is ligated to the second portion 710', which may be a DNA molecule. In this example, the adapter portion 711 may be foreign to the target DNA molecule. Following hybridization, solid phase PCR can be performed to create a population of discrete amplicons, which can then be sequenced to identify the presence of said molecule.

As will be evident to those of skill in the art, the heating mechanisms described herein offer superior performance and functionality when compared to conventional systems. For example, heating reaction chambers using a light absorbing layer (e.g., the layer made up of discrete regions 704 in FIG. 7A) within a reaction vessel housing the reaction chambers (e.g., within or adjacent to the reaction chamber) is significantly more efficient and faster than conventional systems with heaters that are external to the reaction vessel. This is partly because, unlike these conventional systems, the disclosed heating mechanism does not require heat energy to penetrate multiple layers of material to reach the solution within the reaction chambers. The disclosed heating mechanism also ensures more uniform heating, since the amount of heat dissipated to the housing is minimized, thereby ensuring a more uniform delivery of heat. The disclosed heating mechanism also allows for more controlled heating, since, as disclosed elsewhere herein, an amount of light energy delivered to each discrete region may be controlled (e.g., by modulating energy levels of energy sources corresponding to the discrete regions), and/or an amount of light energy absorbed by each discrete region may be controlled (e.g., by adjusting properties such as composition and thickness of the discrete region). This level of control may be particularly useful for applications where primers having different temperature requirements are used. For example, referencing FIG. 7B, the primer 710 may require a first temperature for hybridization, while the primers 711 may require a second temperature for hybridization. The disclosed heating mechanism can easily accommodate this difference by ensuring that the discrete region 704 to which the primer 710 is bound is heated to the first temperature and that the discrete region 704 to which the primer 711 is bound is heated to the second temperature.

Figure 8:
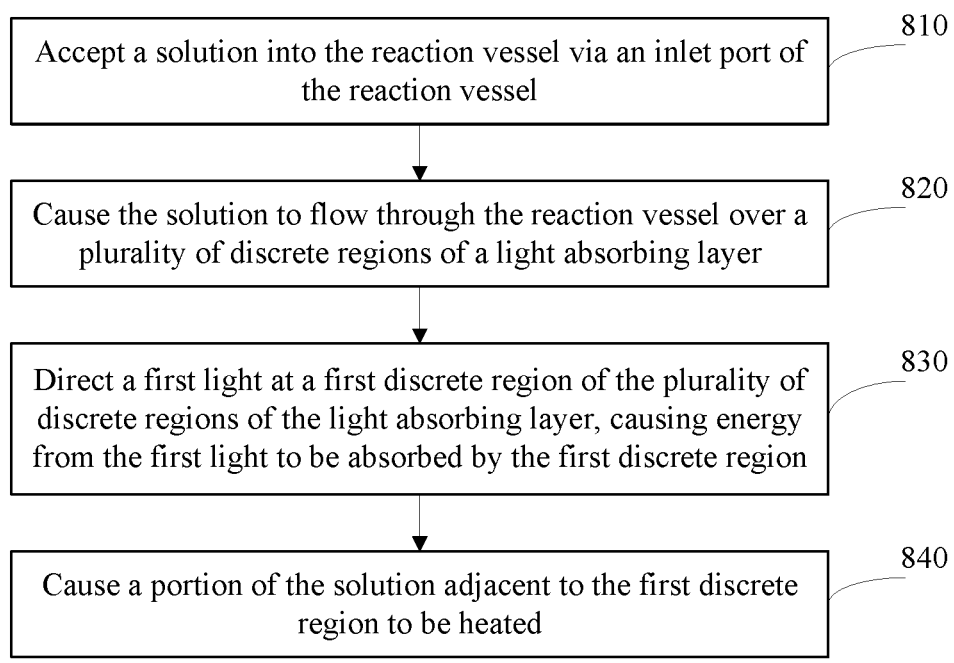
FIG. 8 illustrates an example method 800 for operating a reaction vessel.

FIG. 8 illustrates an example method 800 for operating a reaction vessel. The method may begin at step 810, where a solution may be accepted into the reaction vessel via inlet port of the reaction vessel. At step 820, the solution may be caused to flow around the reaction vessel over a plurality of discrete regions of a light absorbing layer. At step 830, a first light may be directed at a first discrete region of the plurality of discrete regions of the light absorbing layer, causing energy from the first light to be absorbed by the first discrete region. At step 840, a portion of the solution adjacent to the first discrete region may be caused to be heated. Although not illustrated in FIG. 8, it is to be understood that this disclosure contemplates the cooling of discrete regions as well (e.g., by turning off a light source that emits the first light), which may be employed, for example, in multi-step reactions that employ different temperatures for different steps.

Particular embodiments may repeat one or more steps of the method of FIG. 8, where appropriate. Although this disclosure describes and illustrates particular steps of the method of FIG. 8 as occurring in a particular order, this disclosure contemplates any suitable steps of the method of FIG. 8 occurring in any suitable order. Moreover, although this disclosure describes and illustrates an example method for operating a reaction vessel, including the particular steps of the method of FIG. 8, this disclosure contemplates any suitable method for operating a reaction vessel, including any suitable steps, which may include all, some, or none of the steps of the method of FIG. 8, where appropriate. Furthermore, although this disclosure describes and illustrates particular components, devices, or systems carrying out particular steps of the method of FIG. 8, this disclosure contemplates any suitable combination of any suitable components, devices, or systems carrying out any suitable steps of the method of FIG. 8

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

What is claimed is:

1. A reaction vessel, comprising:
an inlet port for accepting a solution into a reaction chamber, wherein the reaction chamber is defined by one or more walls forming an outer perimeter;
a light absorbing layer comprising a plurality of discrete regions disposed on a surface of the outer perimeter, wherein each of the plurality of discrete regions are separated by gaps between each of the discrete regions, wherein the discrete regions are configured to absorb light energy from an energy source, and wherein the discrete regions are fluidically coupled such that the solution is not inhibited by a physical barrier from flowing from the inlet port to an outlet, wherein a portion of the plurality of discrete regions are disposed on a bottom wall of the reaction chamber;
the outlet port for removing the solution from the reaction vessel; and
an optical sensor configured to take readings of the solution within the reaction chamber through the gaps between the plurality of discrete regions; and
a light source disposed below the reaction chamber, wherein the light source is configured to irradiate one or more of the discrete regions through the bottom wall of the reaction chamber.

2. The reaction vessel of claim 1, wherein the light absorbing layer comprises a thin metallic film deposited onto an interior-facing surface of the reaction vessel such that the discrete regions are configured to directly contact the solution.

3. The reaction vessel of claim 1, further comprising a substrate that overlays the light absorbing layer such that the solution does not directly contact the discrete regions.

4. The reaction vessel of claim 1, wherein the plurality of discrete regions comprise a first discrete region and a second discrete region, wherein the first discrete region comprises a first metallic film and the second discrete region comprises a second metallic film, wherein the first metallic film is thicker than the second metallic film, such that the first discrete region has a different temperature profile from the second discrete region.

5. The reaction vessel of claim 1, wherein the plurality of discrete regions comprise a first discrete region and a second discrete region, wherein the first discrete region comprises a first metallic film and the second discrete region comprises a second metallic film, wherein the first metallic film is of a first composition having a first temperature profile and the second metallic film is of a second composition having a second temperature profile, and wherein the first temperature profile is different from the second temperature profile.

6. The reaction vessel of claim 1, wherein the reaction vessel is defined at least in part by a top housing component and a bottom housing component, wherein the plurality of discrete regions comprise a plurality of top discrete regions deposited onto an interior-facing surface of the top housing component and a plurality of bottom discrete regions deposited onto an interior-facing surface of the bottom housing component.

7. The reaction vessel of claim 6, wherein a particular top discrete region is disposed in direct opposition to a particular bottom discrete region, such that molecules in a portion of the solution are thermally confined within an area defined by the particular top discrete region and the particular bottom discrete region when the particular top discrete region and the particular bottom discrete region are heated to a threshold temperature.

8. The reaction vessel of claim 1, wherein a first discrete region of the plurality of discrete regions comprises a gold film, and wherein the first discrete region is configured to bind one or more nucleotide sequences via weak covalent interactions.

* * * * *